United States Patent
Yoshida et al.

(10) Patent No.: US 9,920,098 B2
(45) Date of Patent: *Mar. 20, 2018

(54) PROTEIN LIGAND FOR AFFINITY ISOLATION MATRIX

(71) Applicant: Kaneka Corporation, Osaka (JP)

(72) Inventors: Shinichi Yoshida, Takasago (JP); Dai Murata, Takasago (JP); Fuminori Konoike, Takasago (JP); Keita Iguchi, Takasago (JP); Tomoyuki Nakaishi, Takasago (JP); Masahiro Hayashi, Takasago (JP)

(73) Assignee: KANEKA CORPORATION, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/429,819

(22) PCT Filed: Sep. 24, 2013

(86) PCT No.: PCT/JP2013/075656
§ 371 (c)(1),
(2) Date: Mar. 20, 2015

(87) PCT Pub. No.: WO2014/046278
PCT Pub. Date: Mar. 27, 2014

(65) Prior Publication Data
US 2016/0168209 A1    Jun. 16, 2016

(30) Foreign Application Priority Data
Sep. 21, 2012   (JP) .................. 2012-208762

(51) Int. Cl.
| | |
|---|---|
| B01D 15/38 | (2006.01) |
| B01J 20/26 | (2006.01) |
| C07K 1/22 | (2006.01) |
| C07K 14/31 | (2006.01) |
| C07K 16/06 | (2006.01) |
| C07K 17/00 | (2006.01) |
| C07K 16/00 | (2006.01) |
| C07K 16/12 | (2006.01) |
| C07K 17/12 | (2006.01) |

(52) U.S. Cl.
CPC .......... *C07K 14/31* (2013.01); *B01D 15/3809* (2013.01); *C07K 1/22* (2013.01); *C07K 16/00* (2013.01); *C07K 16/065* (2013.01); *C07K 16/1271* (2013.01); *C07K 17/00* (2013.01); *C07K 17/12* (2013.01); *B01J 2220/4856* (2013.01); *C07K 2317/21* (2013.01); *C07K 2317/52* (2013.01); *C07K 2317/92* (2013.01)

(58) Field of Classification Search
CPC ....... B01D 15/3809; B01J 20/22; B01J 20/24; B01J 20/262; B01J 20/286; B01J 20/289; B01J 2220/4856; C07K 1/22; C07K 14/195; C07K 14/31; C07K 16/065; C07K 17/00; C07K 17/12
See application file for complete search history.

(56) References Cited

U.S. PATENT DOCUMENTS

| | | | |
|---|---|---|---|
| 6,013,763 A | 1/2000 | Braisted et al. | |
| 9,284,354 B2* | 3/2016 | Yoshida | C07K 14/47 |
| 2008/0108564 A1* | 5/2008 | Holmes | C07K 14/505 |
| | | | 514/7.7 |
| 2009/0299035 A1* | 12/2009 | Iwakura | C07K 14/31 |
| | | | 530/324 |
| 2010/0158847 A1* | 6/2010 | Fahnestock | A61K 8/64 |
| | | | 424/70.6 |
| 2010/0286373 A1* | 11/2010 | Majima | B01J 20/286 |
| | | | 530/387.2 |
| 2012/0208234 A1 | 8/2012 | Yoshida et al. | |
| 2013/0096276 A1 | 4/2013 | Yoshida et al. | |
| 2014/0107315 A1* | 4/2014 | Yoshida | C07K 14/31 |
| | | | 530/324 |

FOREIGN PATENT DOCUMENTS

| | | |
|---|---|---|
| EP | 1992692 A1 | 11/2008 |
| EP | 2690173 A1 | 1/2014 |
| JP | 2007-252368 A | 10/2007 |
| JP | 2008-115151 A | 5/2008 |
| JP | 2008-266219 A | 11/2008 |

(Continued)

OTHER PUBLICATIONS

Yoshida et al. Rational design and engineering of protein A to obtain the controlled elution profile in monoclonal antibody purification. Chem-Bio Informatics Journal. 2012. vol. 12, pp. 1-13.*
Hober et al., "Protein A chromatography for antibody purification", Journal of Chromatography B, 848 (2007) 40-47.
Low et al., "Future of antibody purification", Journal of Chromatography B, 848 (2007) 48-63.
Roque et al., "Affinity-based methodologies and ligands for antibody purification: Advances and perspectives", Journal of Chromatography A, 1160 (2007) 44-55.
Wong et al., "Selective Covalent Protein Immobilization: Strategies and Applications", Chem. Rev. 2009, 109, 4025-4053.
Ljungquist et al., "Thiol-directed immobilization of recombinant IgG-binding receptors", Eur. J. Biochem. 186, 557-561 (1989).
English translation of International Preliminary Report on Patentability dated Mar. 24, 2015 in PCT/JP2013/075656.

(Continued)

*Primary Examiner* — Jeffrey E. Russel
(74) *Attorney, Agent, or Firm* — Polsinelli PC

(57) ABSTRACT

An object of the present invention is to develop techniques to create novel engineered protein ligands that maximize the binding capacity and binding efficiency to a target molecule of affinity separation matrices on which the protein ligands are immobilized. The present invention provides protein ligands (variants) that can be immobilized on carriers in a manner shown in schematic FIG. 1(4)-(15), as well as antibody affinity separation matrices obtained by immobilizing such a protein ligand on a water-insoluble carrier. The affinity separation matrices are characterized by their excellent binding capacity and binding efficiency to a target molecule.

14 Claims, 2 Drawing Sheets

(56) References Cited

FOREIGN PATENT DOCUMENTS

| WO | WO-1997/017361 A1 | 5/1997 |
| WO | WO-2008/044692 A1 | 4/2008 |
| WO | WO-2010/110288 A1 | 9/2010 |
| WO | WO-2011/118699 A1 | 9/2011 |
| WO | WO-2012/133349 A1 | 10/2012 |

OTHER PUBLICATIONS

Francesca Scaramozzini et al., Improvement of Catalytic Properties of *Escherichia coli*Penicillin G Acylase Immobilized on Glyoxyl Agarose by Addition of a Six-Amino-Acid Tag, Applied and Environmental Microbiology, Dec. 2005, vol. 71, No. 12, pp. 8937-8940.
International Preliminary Report on Patentability (Chapter 1) issued in PCT/JP2012/057824, dated Oct. 2, 2013, English translation.
www.russelllab.org/aas/lys.html, Lysine, pp. 1-2, published online Oct. 1, 2002.
The On-Line Medical Dictionary, Definition of Derivative, p. 3, published online Nov. 18, 1997.
Sokalingam et al., "A Study on the Effect of Surface Lysine to Arginine Mutagenesis on Protein Stability and Structure Using Green Fluorescent Protein", PLoS ONE 7(7): e40410. doi:10.1371/journal.pone.0040410, Jul. 2012.

\* cited by examiner

PROTEIN LIGAND FOR AFFINITY ISOLATION MATRIX

CROSS REFERENCE TO RELATED APPLICATIONS

This application is a National Phase filing under 35 U.S.C. § 371 of PCT/JP2013/075656 filed on Sep. 24, 2013; and this application claims priority to Application No. 2012-208762 filed in Japan on Sep. 21, 2012 under 35 U.S.C. § 119.

TECHNICAL FIELD

The present invention relates to proteins capable of specifically binding to a target substance, ligand affinity separation matrices obtained by immobilizing such a protein on a carrier, and separation and purification methods using the matrices.

BACKGROUND ART

One of important abilities of proteins is to specifically bind to a particular molecule. Due to this ability, some proteins play important roles in immunoreactions or signal transduction in vivo. Methods for separation and purification of useful substances utilizing this ability are also being actively developed. One example of such methods actually used in industrial applications is Protein A affinity separation matrices that are used to purify (capture) antibody drugs from animal cell cultures at one time at high purity levels.

Antibody drugs developed so far are generally monoclonal antibodies, which are mass-produced by recombinant cell culture techniques or the like. The term "monoclonal antibodies" refers to antibodies that are produced by clones of a unique antibody-producing cell. Almost all the antibody drugs currently available on the market are classified into immunoglobulin. G (IgG) subclasses based on their molecular structures. Protein A is a cell wall protein produced by the gram-positive bacterium *Staphylococcus aureus*, and contains a signal sequence S, five immunoglobulin-binding domains (B domain, D domain, A domain, B domain, and C domain), and a cell wall-anchoring domain known as XM region (Non Patent Literature 1). In the initial purification step (capture step) in the manufacture of antibody drugs, affinity chromatography columns obtained by immobilizing Protein. A as a ligand on a water-insoluble carrier are commonly used (Non Patent Literatures 1 to 3).

Various techniques for improving the performance of Protein A columns have been developed. Technological developments in ligands are also being made. Initially, wild-type Protein A has been used as a ligand, and currently, Protein A variants that have been modified by protein engineering are used as ligands in many techniques for improving the column performance. Notably, some of the Protein. A engineering techniques developed so far focus on now to immobilize Protein A ligands on water-insoluble carriers.

Proteinic ligands including Protein A are each immobilized on a carrier at multiple sites by covalent bonding of the reactive side chain functional groups of lysine (Lys) or cysteine (Cys) residues (which are not present in Protein. A) in the proteins in a manner shown in FIG. 1(1) (Non Patent Literature 4). A recombinant Protein A which has been modified to have a different ratio between the number of lysine (Lys) residues on the antibody binding face and the number of lysine (Lys) residues on the non-binding face of Protein A (Patent Literature 1) is a technique allowing effective use of the antibody binding domains of the ligand even though it has basically the same immobilization form as shown in FIG. 1(1).

Protein A variants that are Protein A containing a mutation of one cysteine (Cys) residue (Patent Literature 2 and Non Patent Literature 5) are each site-specifically immobilized on a carrier via the Cys residue. Protein A variants containing complete deletions of Lys or Cys residues in the amino acid sequence (Patent Literatures 3 and 4) are techniques that immobilize the protein on a carrier via the N terminal (α-amino group) or C terminal (special tag). These techniques allow a protein ligand to be immobilized on a carrier via the terminal in a manner shown in FIG. 1(2) or (3), and the advantages of these techniques are that the orientation of the ligand can be controlled and that the carrier surface area can be effectively used, as mentioned in these documents.

Thus, developments in techniques for immobilizing a protein ligand to an affinity separation matrix are mainly based on techniques relating to Protein A columns that are required to have high performance because of their high industrial usefulness.

CITATION LIST

Patent Literature

Patent Literature 1: JP 2007-252368 A
Patent Literature 2: WO 1997/017361
Patent Literature 3: JP 2008-115151 A
Patent Literature 4: JP 2008-266219 A

Non Patent Literature

Non Patent Literature 1: Hober S. et al., "J. Chromatogr. B", 2007, 848, pp. 40-47
Non Patent Literature 2: Low D. et al., "J. Chromatogr. B", 2007, 848, pp. 48-63
Non Patent Literature 3: Rogue A. C. A. et al., "J. Chromatogr. A", 2007, 1160, pp. 44-55
Non Patent Literature 4: Wong L. S et al., "Chem. Rev.", 2009, 109, pp. 4025-4053
Non Patent Literature 5: Ljungquist C. et al., "Eur. J. Biochem.", 1989, 186, pp. 557-561

SUMMARY OF INVENTION

Technical Problem

As for the immobilization of proteinic ligands including Protein A to carriers, immobilization at a single site only the terminal region) is advantageous in terms of allowing control of the orientation and effective use of the carrier surface area, but is thought to have a serious problem that the ligands are more likely to leak from the carrier as compared to immobilization at multiple sites. In view of this problem, an object to be solved by the present invention is to develop techniques to create novel engineered proteinic ligands to maximize the binding capacity and binding efficiency to a target molecule of affinity separation matrices obtained by immobilizing such a proteinic ligand on a carrier.

Solution to Problem

In order to achieve the object, the present inventors molecularly designed a large number of recombinant variants of Protein A, acquired these variants by protein engineering techniques and genetic engineering techniques, and compared the physical properties of these variants and the performance of antibody affinity separation matrices obtained by immobilizing such a variant on a water-insoluble carrier. As a result of the investigation, the present inventors found that affinity separation matrices prepared by immobilizing a protein ligand on a carrier in a manner shown in any of FIG. 1(4)-(15) achieve maximal binding capacity and binding efficiency to a target molecule.

Specifically, the present invention relates to a protein, containing two or more amino acid sequences derived from any domain selected from E, D, A, B, and C domains of Protein A, the amino acid sequences having amino acid substitutions for all lysine residues (Lys), wherein the amino acid sequences are connected to one another through one or more linkers, and at least one of the linkers contains a lysine residue (Lys) or a cysteine residue (Cys).

Preferably, at least one of the linkers contains Lys.

Preferably, the amino acid sequence before the substitutions is any of the amino acid sequences of SEQ ID NOs:1 to 5 or any of the amino acid sequences of SEQ ID NOs:1 to 5 comprising at least one of the following mutations (1) to (4):
(1) a substitution of Ala, Val, Leu, Ile, Phe, Tyr, Trp, Thr, Ser, Asp, Glu, Are, His, or Met for an amino acid residue in the domain corresponding to position 29 of the C domain;
(2) a substitution of Leu, Ile, Phe, Tyr, Trp, Thr, Asp, Gin, Asn, Glu, Arg, His, or Met for an amino acid residue in the domain corresponding to position 33 of the C domain;
(3) a substitution of Leu, lie, Phe, Tyr, Trp, Glu, Arg, His, or Met for an amino acid residue in the domain corresponding to position 36 of the C domain; and
(4) a substitution of Len, Ile, Phe, Tyr, Trp, Glu, Arg, His, or Met for an amino acid residue in the domain corresponding to position 37 of the C domain.

Preferably, at least half of all the amino acid substitutions for Lys are substitutions to Arg.

Preferably, all the amino acid substitutions for Lys are substitutions to Arg.

Preferably, at least 90% of the following amino acid residues: Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 (the residue numbers indicated are corresponding residue numbers of the C domain) are conserved in the protein, and the protein has at least 80% sequence identity to the amino acid sequences before the substitutions.

Preferably, the protein contains Lys or Cys at at least one terminal thereof.

Preferably, the protein contains Lys at at least one terminal thereof.

The present invention also relates to a DNA, encoding the protein,

The present invention further relates to a vector, containing the DNA.

The present invention further relates to a transformant, obtained by transforming host cells with the vector.

The present invention also relates to a method for producing the protein, including using either a cell-free protein synthesis system including the DNA or the vector, or the transformant.

The present invention further relates to an affinity separation matrix, including: the protein as an affinity ligand; and a carrier made of a water-insoluble base material on which the protein is immobilized.

The affinity separation matrix preferably binds to a protein containing an Fe region of an immunoglobulin.

The protein containing an Fc region of an immunoglobulin is preferably an immunoglobulin G or an immunoglobulin G derivative.

The present invention further relates to a method for producing the affinity separation matrix, the method including immobilizing the protein as an affinity ligand on a carrier made of a water-insoluble base material.

The present invention further relates to a method for purifying a protein containing an Fc region of an immunoglobulin, the method including adsorbing the protein containing an Fc region of an immunoglobulin to the affinity separation matrix.

The present invention further relates to a method for producing an affinity separation matrix, the method including immobilizing, on a carrier, an affinity ligand in which two or more binding domains that bind to the same target molecule are connected to one another through one or more linkers, wherein the affinity ligand is immobilized on the carrier via at least one amino acid residue present in at least one of the linkers without involving core regions of the binding domains.

Preferably, the affinity ligand is immobilized on the carrier additionally via an N-terminal region and/or a C-terminal region.

Advantageous Effects of Invention

Affinity separation matrices obtained by immobilizing a novel engineered protein ligand according to the present invention on a water-insoluble carrier characteristically have high binding capacity to a target molecule even when the amount of ligand immobilized is small. The techniques of the present invention allow proteins, which are very expensive to produce, to perform at the maximum levels, while the techniques can increase the amount of antibody-containing culture supernatant that can be processed per operation. Accordingly, the techniques provide many industrial benefits to both manufacturers and users of affinity separation matrices.

The novel engineered protein ligands obtained according to the present invention are designed to be immobilized on a carrier in a manner shown in any of schematic FIG. 1(4)-(15). Their immobilization forms are very different from those of the ligands of the prior art. Although the exemplary ligands shown in FIG. 1 are of the three-domain type, ligands of the four-domain type are immobilized in the same manner. The effects of the present invention can be produced with ligands having an increased number of domains.

A notable difference of the present invention from the forma of the prior art is that the ligand is immobilized via at least one interdomain linker region. This feature is expected to cause a great difference in the (global) configuration and dynamic behavior of the multi-domain ligand between when the ligand is immobilized on a carrier in the solid phase) and when the ligand is not immobilized on the carrier (in the liquid phase). Further, the amino acid residues in the core regions of the individual domains are not involved in immobilization on a carrier. Thus, it is expected that the configuration and dynamic behavior of the individual domains will not change between when the ligand is immobilized on a carrier and when it is not immobilized.

Then, it has been surprisingly found that the affinity separation matrices of the present invention have significantly improved binding capacity to an antibody as compared to the forms shown in FIG. 1(1) and (2).

Thus, since the ligand according to the present invention is immobilized on a carrier at multiple immobilization sites, this immobilization manner can provide benefits such as preventing the ligand from easily leaking from the carrier while improving the binding capacity to a target molecule.

DESCRIPTION OF EMBODIMENTS

Figure 1:
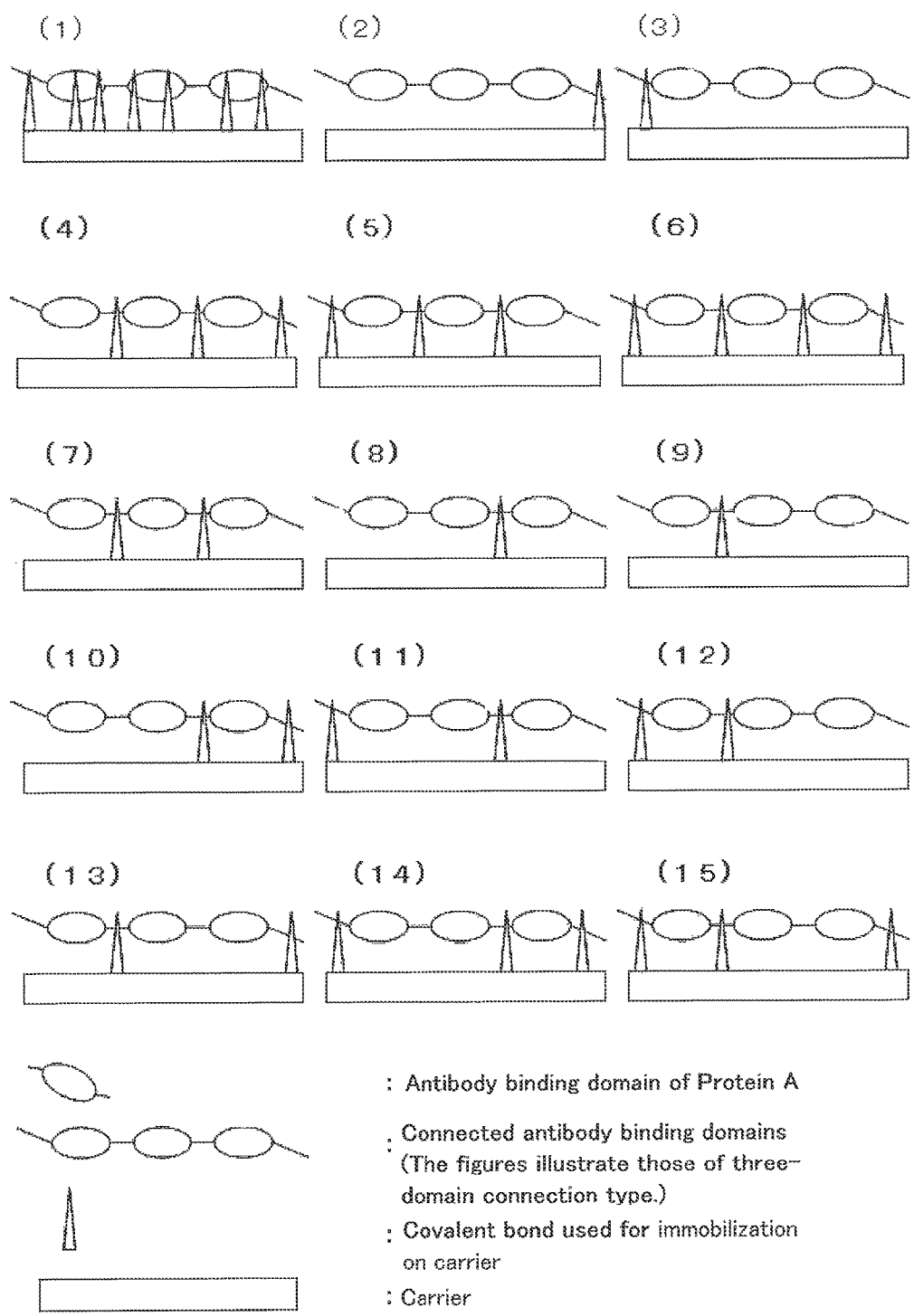
FIGS. 1(1) through (15) are views each schematically illustrating a form in which a protein ligand of the present invention is immobilized on a carrier.

The amino acid substitutions herein are expressed using the code for the wild-type or non-mutated type amino acid followed by the position number of the substitution and followed by the code for changed amino acid. For example, a substitution of Ala for Gly at position 29 is represented by G29A.

The term "protein." used herein is intended to include any molecule of polypeptide structure and thus include fragmented polypeptide chains and polypeptide chains linked through peptide bonds as well. The term "domain" refers to a conformational unit of a protein which has a sequence consisting of several tens to hundreds of amino acid residues, and sufficiently, fulfills a certain physicochemical or biochemical function, The term "affinity ligand" refers to a substance that is capable of selectively capturing (binding to) a target molecule in a mixture of molecules due to a specific affinity between molecules, such as, typically, antigen-antibody binding. The term "ligand" as used alone herein is synonymous with the "affinity ligand".

The affinity ligand according to the present invention is a multimeric protein (multi-domain protein) in which two or more, preferably 2 to 10, more preferably 2 to 8, still more preferably 2 to 6, most preferably 3 to 6, target molecule-binding domains (monomeric proteins or single domains) are connected together. The multimeric protein may be a homopolymer (e.g. homodimers, homotrimers) consisting of connected target molecule-binding domains of the same type, or may be a heteropolymer (e.g. heterodimers, heterotrimers) consisting of connected target molecule-binding domains of different types as long as their target molecules are the same.

In the present invention, the target molecule-binding domains are connected to one another through one or more linkers. Preferably, they are connected through the linkers in a manner that does not destabilize the three-dimensional structure of the individual monomeric proteins.

In one embodiment, a protein of the present invention as a proteinic component may be fused with another protein having a different function. Examples of fusion proteins include, but are not limited to, fusion proteins with albumin or GST (glutathione S-transferase). Additionally, fusion proteins with a nucleic acid (e.g. a DNA aptamer), a drug (e.g. an antibiotic) or a polymer (e.g. PEG (polyethylene glycol)) are also included within the scope of the present invention, provided that they take advantage of the benefits of proteins according to the present invention.

Examples of active groups that can be present in the protein and involved in immobilization of the protein on a carrier include, but not limited to, an amino group of the N-terminal amino acid, an amino group of a side-chain lysine (Lys), a thiol group of a side-chain cysteine (Cys), a carboxyl group of the C-terminal amino acid, and a carboxyl group of a side-chain glutamic acid (Glu) or side-chain aspartic acid (Asp) (Non Patent Literature 4).

The "amino acid residue(s) to be involved in a reaction of immobilization on a carrier" are, for example, the N-terminal amino acid and lysine residues when an amino group is used as a functional group that participates in the immobilization reaction. In the case where the ε-amino group of lysine alone is used as a functional group that participates in the immobilization reaction due to the difference in pKa, only the lysine residue corresponds to the above-mentioned amino acid residue. Specifically, the proteins obtained according to the present invention are premised on being immobilized on a carrier before use, which means that the "amino acid residue(s) to be involved in a reaction of immobilization on a carrier" depend uniquely on the particular reaction of immobilization on a carrier. From the standpoint of reactivity, the amino acid to be involved in the immobilization is preferably lysine or cysteine. The functional group is preferably the amino group of lysine or the thiol group of cysteine. Since proteins containing cysteine tend to form a dimer, the "amino acid residue(s) to be involved in a reaction of immobilization on a carrier" are more preferably lysine residue(s) because such proteins are easy to handle.

The term "interdomain linker region" refers to a connection between target-binding domains connected together, in other words, a region formed by connecting a C-terminal region of a domain sequence on the N-terminal side and an N-terminal region of a domain sequence on the C-terminal side. In the case of a protein containing N domains connected in tandem, the number of linker regions is N−1. Thus, the "interdomain linker region" herein is defined as a region consisting of at least two amino acid residues, including the C-terminal amino acid residue of a domain on the N-terminal side and the N-terminal amino acid residue of a domain on the C-terminal side.

As described above, the linker region may contain one or more amino acid residues other than those of the domain sequences. The number of amino acid residues in the linker region is preferably 16 or less residues, more preferably 8 or less residues, and still more preferably 4 or less residues. The linker preferably contains lysine or cysteine, and more preferably contains lysine.

The "N-terminal region" and "C-terminal region" herein each preferably consist of 8 or less residues, more preferably 4 or less residues, still more preferably 2 or less residues, and further more preferably 1 or less residues (so-called N terminal or C terminal) The proteins of the present invention may contain lysine or cysteine at at least one terminal thereof.

The term "core region" as used herein refers to, with respect to each of the individual domain sequences connected, all the regions, except the N-terminal region and C-terminal region. Since, two or more domains are connected in the present invention, the "core regions" also refers to all the regions, except the individual interdomain linker regions, the N-terminal region of the protein (the N-terminal region of the most N-terminal domain) and the C-terminal region of the protein (the C-terminal region of the most C-terminal domain).

From another standpoint, the N-terminal and C-terminal regions of the domains herein can be defined as regions at both ends of the domains that do not assume a particular secondary structure. Specifically, the N-terminal and C-terminal regions are more flexible (movable) than regions having a specific secondary structure. The term "secondary structure" as used herein includes, but not limited to, α-helices, β-strands (sheets), and turns.

The secondary structure of target-binding domains can be determined based on data on the conformation of the same or similar amino acid sequences. Data on the conformation of the amino acid sequences are available from, for example, RCSB Protein Data Bank (www.rcsb.org/pdb/home/home.do). Alternatively, a program for secondary structure assignment such as DSSP (swift.cmbi.ru.nl/gv/dssp/) may be used to estimate the secondary structure, or spectroscopic techniques (e.g. X-ray or NMR analysis) may be performed to experimentally obtain the secondary structure.

Even if such data are difficult to obtain, it is apparent that the N-terminal and C-terminal amino acids of the domains (protein) are highly flexible. Thus, the proteins of the present invention essentially include the "N-terminal region" and the "C-terminal region" each consisting of at least one amino acid residue, and further include the "linker region(s)" consisting of two or more amino acid residues (the C-terminal amino acid of one domain and the N-terminal amino acid of another domain).

The effects of the present invention can be produced even when the amino acid residue(s) to be involved in immobilization of the ligand on a carrier are displaced by approximately several residues within the region.

The present invention also relates to a method for producing an affinity separation matrix which includes immobilizing, on a carrier, an affinity ligand in which two or more binding domains that bind to the same target molecule are connected to one another through one or more linkers, wherein the affinity ligand is immobilized on the carrier via at least one amino acid residue present in at least one of the linkers without involving core regions of the binding domains. Preferably, the affinity ligand is immobilized on the carrier additionally via an N-terminal region and/or a C-terminal region. The affinity ligand is a protein in which: (A) at least one of the interdomain linker regions of the protein contains at least one amino acid residue to be involved in a reaction of immobilization on a carrier; (B) the N-terminal region and/or the C-terminal region of the protein may contain an amino acid residue to be involved in the reaction of immobilization; and (C) the core regions of the individual domains of the protein are free from amino acid residues to be involved in the reaction of immobilization. The following provides a supplemental description of the protein by means of an example of a protein including three target molecule-binding domains connected together.

For ease of reference, the "protein including three target molecule-binding domains connected together" is referred to as "three-domain type", and the "amino acid residue(s) to be involved in a reaction of immobilization on a carrier" is referred to as "residue(s) for immobilization". According the definition herein, the three-domain type includes two linker regions.

Thus, since the protein obtained according to the present invention satisfies the condition (A), the linker regions contain at least one residue for immobilization. In other words, the residue for immobilization is present in any of the following manners: (a) the residue for immobilization is present only in the linker region on the N-terminal side, or (b) only in the linker region on the C-terminal side, or (c) in both the linker regions. Preferably, the residue for immobilization is present in both the linker regions.

As for the condition (B), the following four manners (d) to (g) may be contemplated: (d) the residue for immobilization is present only in the N-terminal region of the three-domain type; or (e) only in the C-terminal region thereof; or (f) in both the N-terminal region and the C-terminal region; and (g) the residue for immobilization is present neither in the N-terminal region nor in the C-terminal region.

Moreover, since the condition (C) is satisfied, the residue for immobilization is not present in the protein in a manner other than those mentioned above. Referring to FIG. 1, if the protein is of a three-domain type in which linker/terminal region(s) include (s) one residue for immobilization, the protein may be in any of the forms shown by FIG. 1(4)-(15).

The number of residues for immobilization in each of the individual linker regions (or the N-/C-terminal region) is preferably 1 to 8, more preferably 1 to 4, still more preferably 1 to 2, and further more preferably 1.

In terms of preventing ligand leak, the number of residues for immobilization (per molecule of the multi-domain type) in the protein is preferably larger. Provided that the number of domains in the protein is N, the number of residues for immobilization is preferably at least N−2, more preferably at least N−1, and still more preferably at least N.

In the present invention, the target molecule for the affinity ligand may be any molecule to which the target molecule-binding domains can bind, and mention may be made of, for example, proteins containing an Fc region of an immunoglobulin. Specific examples include immunoglobulin G (IgG) and immunoglobulin G derivatives.

The term "immunoglobulin G derivative" as used herein is a generic name of engineered artificial proteins, including, for example, chimeric immunoglobulin Gs in which the domains of human IgG are partially replaced and fused with IgG domains of another biological species, humanized immunoglobulin Gs in which the complementarity determining regions (CDRs) of human IgG are replaced and fused with antibody CDRs of another biological species, immunoglobulin Gs whose Fc region has a molecularly altered sugar chain, and artificial immunoglobulin Gs in which the Fv region and the Fc region of human IgG are fused.

Target molecule-binding domains that are targeted to immunoglobulin G or immunoglobulin G derivatives are included in various immunoglobulin-binding proteins. Examples of the immunoglobulin-binding proteins include, but not limited to, Protein A derived from *Staphylcoccus aureus*, Protein G derived from *Streptococcus* sp. Group C/G, Protein L derived from *Peptostreptococcus ma gnus*, Protein H derived from group A *Streptococcus*, Protein D derived from *Haemophilus influenzae*, Protein Arp derived from *Streptococcus* AP4, and FcγR of human origin.

As immunoglobulin G-binding domains, E, D, A, B, and C domains of Protein A may be mentioned herein. These domains are immunoglobulin-binding proteins capable of binding to regions other than the complementarity determining regions (CDRs) of immunoglobulins, and can bind to any of the Fc and Fab regions of immunoglobulins and particularly the Fv region in the Fab region. In general, the domains more strongly bind to the Fc region than to the Fab (Fv) region (Non Patent Literature 3).

In the present invention, in the case where the amino acid residue(s) to be involved in a reaction of immobilization on a carrier are lysine residue(s), the amino acid sequences of immunoglobulin-binding domains of Protein A, in which all Lys residues, except the terminal Lys, have been substituted with amino acid residues other than Lys need to be connected.

After all the Lys residues including the terminal Lys in the amino acid sequences are substituted with amino acid residues other than Lys, at least one amino acid residue in the terminal regions of the domain sequences may be substituted with Lys before use. Alternatively, as an amino acid other than those in the domain sequences, at least one Lys residue may be added to the linker or terminal regions.

Moreover, in the case where the amino acid residue(s) to be involved in a reaction of immobilization on a carrier are cysteine residue(s), since the immunoglobulin-binding domains of Protein A contain no Cys in their amino acid sequences, amino acid sequences may be obtained by substituting Cys for at least one amino acid residue in the terminal regions of the domain sequences, or by adding at least one Cys residue as an amino acid other than those in the domain sequences to the linker or terminal regions.

Thus, in the present invention, in cases where amino acid residue(s) that can be immobilized on a carrier are present in the amino acid sequences, excluding the terminal regions of the target molecule-binding domains to be connected, the amino acid residue(s) need to be substituted. At this time, it is important to ensure that the binding ability of the target molecule-binding domains to their target molecule is not eliminated by introducing the mutations according to the present invention.

Figure 2:
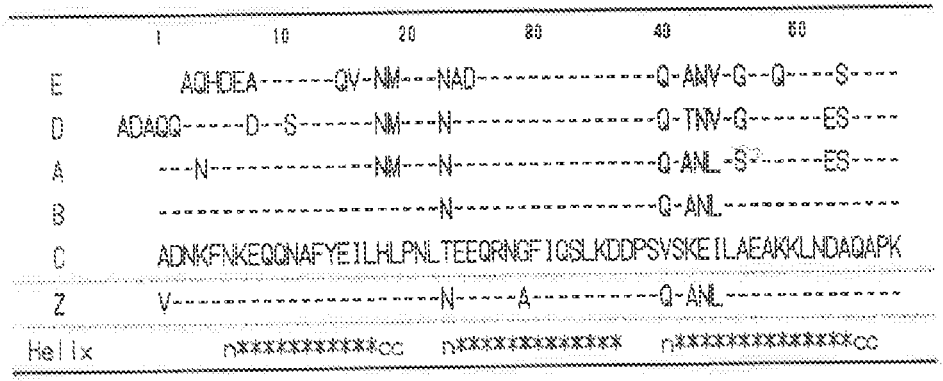
FIG. 2 is a table for comparison of the sequences of E (SEQ ID NO:1), D (SEQ ID NO:2), A (SEQ ID NO:3), B (SEQ ID NO:4), C (SEQ ID NO:5), and Z (SEQ ID NO:6) domains of Protein A.

A specific embodiment of the present invention is described using any of the sequences of E, D, A, B, and C domains of wild-type Protein A as represented by SEQ ID NOs:1 to 5. These domains can be aligned as shown in FIG. 2.

For ease of reference, the C domain (SEQ ID NO:5) is used as a standard below. As for residue number, for example, the residue at position 31 of the C domain corresponds to that at the same position 31 of the A or B domain, position 29 of the E domain, and position 34 of the D domain. For the E, D, A, and B domains of Protein A, the term "all lysine (Lys) residues" refers to 6 Lys residues corresponding to positions 4, 7, 35, 49, 50, and 58 of the C domain. These domains have high sequence identity to one another, and thus can be aligned. For example, Clustal (www.clustal.org/omega/), which is a program for amino acid sequence multiple alignment, may be used for confirmation.

For the C domain of Protein A, the term refers to 7 Lys residues at positions 4, 7, 35, 42, 49, 50, and 58. However, in cases where the amino acid sequence before the mutations is a sequence that already contains one or more deletions, for example, at positions 1 to 4, the number of Lys residues is not limited to the number mentioned above. Moreover, the phrase "all lysine residues, except the terminal lysine" refers to all lysine residues, except Lys corresponding to position 58 of the C domain, when used for the domains of Protein A.

According to the present invention, the C-terminal lysine residue of the C domain is essentially present in the linker region between the connected domains or the C-terminal region of the protein obtained after connection (multi-domain type), Accordingly, this lysine residue may exceptionally not be substituted even when lysine residue(s) are used for immobilization.

In the "amino acid substitutions for Lys residues," the type of amino acid to be introduced by substitution includes, but not limited to, non-proteinogenic amino acids and non-natural amino acids. From the standpoint of production by genetic engineering, natural amino acids can be suitably used.

In addition, at least half of the amino acid substitutions are preferably substitutions to arginine (Arg). More preferably all of them except two, still more preferably all of them except one, further more preferably all of them are substitutions to Arg. This is because Arg is a basic amino acid having similar properties to Lys, and causes a relatively small effect on the properties of the whole protein.

In one specific embodiment of the present invention, the sequence before the mutations according to the present invention may be any of E, D, A, B, and C domain variants of wild-type Protein A. For example, the amino acid sequence called Z domain which is obtained by introducing A1V and G29A mutations into the B domain, as shown as SEQ ID NO:6, is regarded as a sequence derived from the B domain, and, of course, those obtained by introducing the mutations according to the present invention into the Z domain are also included within the scope of the present invention.

The conformation of the Z domain has been determined with high accuracy by NMR spectroscopy. According to this data in combination with the previously known data on the conformation of the B and E domains, α-helical regions of the immunoglobulin C-binding domains of Protein A are identified (Tashiro M. et al., "J. Mol. Biol.", 1997, Vol. 272, pp. 573-590 and PDB code: 2SPZ from RCSB Protein Data Bank).

The alignments shown in FIG. 2 are provided with the sequence of the Z domain, and the assignments of the identified α-helical structures. The symbol "*" indicates α-helices, the symbol "n" indicates the N caps of the helices conserved in the individual domains, and the symbol. "c" indicates the C caps of the helices conserved in the individual domains, Provided that N- and C-terminal sequences that do not assume a particular secondary structure are defined as N- and C-terminal regions of the domains, respectively, as described above, the N-terminal regions of the immunoglobulin G-binding domains of Protein A are each preferably composed of amino acid residues corresponding to positions 1 to 6, more preferably positions 1 to 5 of the C domain (the E and D domains differ in length from the C domain).

Likewise, the C-terminal regions of the immunoglobulin G-binding domains of Protein A are each preferably composed of amino acid residues corresponding to positions 55 to 58, more preferably positions 57 to 58 of the C domain.

When the embodiments of the present invention are considered from another standpoint, the proteins of the present invention contain no amino acid residue that is to be a site for immobilization on a carrier, in the internal domain regions other than the N-terminal and C-terminal regions of the individual domains of the proteins (multi-domain type) including connected domains. The proteins of the present invention contain at least one amino acid residue to be a site for immobilization on a carrier, in regions other than the internal domain regions in the proteins.

The amino acid sequences of the domains before the mutations of the present invention are each preferably any of the amino acid sequences of SEQ ID NOs:1 to 5 or any of the amino acid sequences of SEQ ID NOs:1 to 5 having at least one of the following mutations (1) to (4):

(1) a substitution of Ala, Val, Leu, Ile, Phe, Tyr, Trp, Thr, Ser, Asp, Glu, Arg, His, or Met for an amino acid residue in the domain corresponding to position 29 of the C domain;
(2) a substitution of Leu, Ile, Phe, Tyr, Trp, Thr, Asp, Gin, Asn, Glu, Arg, His, or Met for an amino acid residue in the domain corresponding to position 33 of the C domain;
(3) a substitution of Leu, Ile, Phe, Tyr, Trp, Glu, Arg, His, or Met for an amino acid residue in the domain corresponding to position 36 of the C domain; and
(4) a substitution of Leu, lie, Phe, Tyr, Trp, Glu, Arg, His, or Net for an amino acid residue in the domain corresponding to position 37 of the C domain.

More preferred are amino acid sequences having at least one of the amino acid residue substitutions (5) to (8) shown below:
(5) a substitution of Ala, Glu, or Arg for an amino acid residue in the domain corresponding to position 29 of the C domain;
(6) a substitution of Leu, Thr, or Gin for an amino acid residue in the domain corresponding to position 33 of the C domain;
(7) a substitution of Ile or Arg for an amino acid residue in the domain corresponding to position 36 of the C domain;
(8) a substitution of Leu, Ile, Glu, Arg, or His for an amino acid residue in the domain corresponding to position 37 of the C domain.

In the proteins of the present invention, preferably at least 90%, more preferably at least 95%, of the 20 amino acid residues shown below are conserved.

For example, at least 90% of the following amino acid residues: Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 are preferably conserved (the residue numbers indicated are corresponding residue numbers of the C domain.) At the same time, the whole proteins preferably have at least 80%, more preferably at least 85%, still more preferably at least 90%, and further more preferably at least 95% sequence identity.

The present invention further includes, as one embodiment, affinity separation matrices containing a protein described above as an affinity ligand and a carrier made of a water-insoluble base material on which the ligand is immobilized.

Examples of the carrier made of a water-insoluble base material used in the present invention include inorganic carriers such as glass beads and silica gel; organic carriers such as synthetic polymers (e.g. cross-linked polyvinyl alcohols, cross-linked polyacrylates, cross-linked polyacrylamides, cross-linked polystyrenes) and polysaccharides (e.g. crystalline cellulose, cross-linked celluloses, cross-linked agaroses, cross-linked dextrans); and composite carriers of combinations of these carriers such as organic-organic or organic-inorganic composite carriers. Examples of commercially-available products include GCL2000 (porous cellulose gel), Sephacryl S-1000 (prepared by covalently cross-linking allyl dextran with methylenebisacrylamide), Toyopearl (acrylate carrier), Sepharose CL4B (cross-linked agarose carrier) and Cellufine (cross-linked cellulose carrier). It should be noted that the carriers mentioned above do not limit the range of water-insoluble carriers usable in the present invention in view of the purpose and manner of use of the affinity separation matrices, the water-insoluble carrier used in the present invention desirably has a large surface area, and is preferably a porous carrier having a large number of fine pores of an appropriate size. The carrier may be in any form such as beads, monolith, fiber, or film (including hollow fiber), and the form may be chosen as appropriate.

In the case where the amino acid residue(s) to be involved in a reaction of immobilization of the affinity ligand on the carrier are lysine residue(s), the ligand may be immobilized by any method, without particular limitation, as long as the ligand is covalently bonded to the carrier via the ϵ-amino group of lysine in the ligand by a conventional coupling method.

Moreover, even if some of the ligand molecules turn out to be immobilized on the carrier via the α-amino group at the N terminal, such cases in which they are immobilized at the protein N terminal are also within the scope of the present invention.

Examples of such coupling methods include an immobilization method including reacting the carrier with cyanogen bromide, epichlorohydrin, diglycidyl ether, tosyl chloride, tresyl chloride, hydrazine, sodium periodate, or the like to activate the carrier (or introduce a reactive functional group into the carrier surface), followed by a coupling reaction with a compound to be immobilized as the ligand; and an immobilization method including condensation and cross-linking by adding a condensation reagent such as carbodiimide or a reagent containing a plurality of functional groups in the molecule, such as glutaraldehyde, to a system containing the carrier and a compound to be immobilized as the ligand.

In the case where the amino acid residue(s) to be involved in a reaction of immobilization on the carrier are cysteine residue(s), the ligand may be immobilized by any method, without particular limitation, as long as the ligand is covalently bonded to the carrier via the thiol group of cysteine in the ligand by a conventional coupling method.

Likewise, as an example of a coupling method, mention may be made of a method including reacting the carrier with epichlorohydrin or the like to activate the carrier, followed by a coupling reaction with a compound to be immobilized as the ligand. A spacer molecule consisting of a plurality of atoms may also be introduced between the ligand and the carrier, or alternatively, the ligand may be directly immobilized on the carrier.

Purification of target molecules using the affinity separation matrices can be accomplished by procedures according to common affinity column chromatographic purification techniques. In the case where, for example, immunoglobulin G is a target molecule, purification can be accomplished by procedures in accordance with the affinity column chromatographic purification techniques using a Protein. A column that is already commercially available (Non Patent Literature 3).

Specifically, a buffer containing a protein containing an Fc region of an immunoglobulin is prepared as a neutral solution, which is then passed through an affinity column filled with an affinity separation matrix of the present invention so that the protein containing an Fe region of an immunoglobulin is adsorbed on the affinity separation matrix.

Next, an adequate amount of a pure buffer is passed through the affinity column to wash the inside of the column. At this time, the target protein containing an Fc region of an immunoglobulin remains adsorbed on the affinity separation matrix of the present invention in the column.

Subsequently, an acidic buffer adjusted to an appropriate pH is passed through the column to elute the target protein containing an Fc region of an immunoglobulin. Thus, high-level purification can be achieved. Without being limited to such acid buffers, any solution that contains an agent that promotes the target molecule to dissociate from the matrix may be used for elution of the target molecule.

The affinity separation matrices of the present invention can be reused by passing a pure buffer (in some cases, a solution containing an appropriate modifier or organic solvent) having an adequately strong acidity or alkalinity which does not completely impair the functions of the ligand compound and the carrier base material through the matrices to wash them.

The present invention also relates to DNAs having a base sequence encoding any of the proteins described above. The base sequence encoding any of the proteins may be any base sequence that can be translated into any of the amino acid sequences of the proteins. DNAs having such base sequences can be obtained by common known methods, for example, by using a polymerase chain reaction (hereinafter, abbreviated as PCR).

The DNAs may also be synthesized by known chemical synthesis methods, or are available from DNA libraries. The codons in the base sequences may be replaced with degenerate codons, and the base sequences need not to be the same as the original base sequences, provided that they are translated into the same amino acids as those encoded by the original base sequences Recombinant DNAs containing one or more of such a sequence, or the recombinant DNAs in the form of plasmids or phages, as well as transformed microorganisms/cells transformed with vectors containing such a DNA, or genetically engineered microorganisms containing such a DNA, or cell-free protein synthesis systems including such a DNA as a template DNA for transcription are usable.

Moreover, the proteins of the present invention can be obtained as fusion proteins with known proteins that help protein expression or facilitate purification. In other words, microorganisms or cells containing at least one recombinant DNA encoding a fusion protein containing any of the proteins of the present invention can be obtained. Examples of such proteins include, but are not limited to, maltose-binding protein (MBP) and glutathione S-transferase (GST), Site-directed mutagenesis for modifying DNAs encoding the proteins of the present invention can be carried out using recombinant DNA techniques, PCR or the like as follows.

Specifically, mutagenesis by recombinant DNA techniques may be carried out by, for example, cassette mutagenesis in which when there are appropriate restriction enzyme recognition sequences on both sides of a mutagenesis target site in a gene encoding a protein of the present invention, a region containing the mutagenesis target site is removed by cleaving these restriction enzyme recognition sequences with the restriction enzymes, and then a DNA fragment that has been mutated only at the target site by chemical synthesis or the like, is inserted.

Alternatively, site-directed mutagenesis by PCR may be carried out by, for example, a double primer method in which PCR is performed using a double-stranded plasmid encoding the protein as a template, and two types of synthetic oligo primers containing a mutation, complementary to the + and − strands.

Alternatively, a DNA encoding a multimeric protein may be prepared by ligating a desired number of DNAs encoding a monomeric protein (single domain) according to the present invention in tandem. For example, the ligation to produce a DNA encoding a multimeric protein may be accomplished by introducing an appropriate restriction enzyme site into the DNA sequence, fragmenting the DNA sequence with the restriction enzyme, and ligating the double-stranded DNA fragments using a DNA ligase. Only one restriction enzyme site may be introduced, or different types of restriction enzyme sites may be introduced.

The method for preparing a. DNA encoding a multimeric protein is not limited to such ligation methods. For example, such DNAs may be prepared by applying the aforementioned mutagenesis methods to a DNA encoding Protein A (for example, see NO 2006/004067). If the base sequences encoding the respective monomeric proteins in the DNA encoding a multimeric protein are the same, homologous recombination may be caused in host cells. For this reason, the ligated DNAs encoding the respective monomeric proteins preferably have 90% or lower base sequence identity, and more preferably 85% or lower base sequence identity to one another.

The "expression vectors" of the present invention contain a base sequence encoding any of the proteins described above or a partial amino acid sequence thereof and a promoter that is operably ligated to the base sequence to function in host cells. Typically, these vectors can be constructed by ligating or inserting a gene encoding any of the proteins described above into an appropriate vector. The vector into which the gene is inserted is not particularly limited, provided that it is capable of autonomous replication in host cells. The vector may be a plasmid DNAs or a phage DNA.

For example, in the case of using *Escherichia coli* host cells, examples of the vector include pQE vectors (QIAGEN), pET vectors (Merck), and pGEX vectors (GE Healthcare Bio-Sciences).

Examples of plasmid vectors useful for gene expression in *Brevibacillus* host cells include the known *Bacillus subtilis* vector pUB110 and pHY500 (JP H02-31682 A), pNY700 (JP H04-278091 A), pNU211R2L5 (JP H07-170984 A), and pHT210 (JP 1106-133782 A), and the shuttle vector pNCMO2 for *Escherichia coli* and *Brevibacillus* bacteria (JP 2002-238569 A).

The transformants of the present invention are obtainable by transfection of a recombinant vector of the present invention into host cells. The recombinant DNA may be transfected into host cells by, for example, but not limited to, a method using calcium ions, an electroporation method, a spheroplast method, a lithium acetate method, an *Agrobacterium* infection method, a particle gun method, or a polyethylene glycol method.

The function of the obtained gene may also be expressed in host cells by, for example, a method of incorporating the gene obtained in the present invention into the genome (chromosome).

The host cells are not particularly limited, and examples suitable for low-cost mass production are *Escherichia coli*, *Bacillus subtilis* and bacteria (eubacteria) of genera including *Brevibacillus, Staphylococcus, Streptococcus, Streptomyces,* and *Corynebacterium*. Examples of *Brevibacillus* bacteria include *Brevibacillus choshinensis*.

The proteins of the present invention may be produced by culturing any of the transformants in a medium to produce and accumulate the protein of the present invention in the cultured cells (including the periplasmic space thereof) or in the culture fluid (extracellularly), and collecting the desired protein from the culture.

Alternatively, the proteins of the present invention may be produced by culturing any of the transformants in a medium to produce and accumulate a fusion protein containing the protein of the present invention in the cultured cells (including the periplasmic space thereof) or in the culture fluid (extracellularly), collecting the fusion protein from the culture, cleaving the fusion protein with an appropriate protease, and collecting the desired protein.

The transformants of the present invention may be cultured in media in accordance with common methods for culturing host cells. The media that can be used for culturing the obtained transformants are not particularly limited, provided that they allow for high-efficiency, high-yield production of the proteins. Specifically, carbon and nitrogen sources such as glucose, sucrose, glycerol, polypeptone, meat extracts, yeast extracts, and casamino acids may be used, In addition, the media may optionally be supplemented with inorganic salts such as potassium salts, sodium salts, phosphates, magnesium salts, manganese salts, zinc salts, and iron salts. In the case of using auxotrophic host cells, nutritional substances necessary for their growth may be added to the media. Moreover, antibiotics such as penicillin, erythromycin, chloramphenicol, and neomycin may optionally be added.

Furthermore, in order to inhibit degradation or molecular size reduction of the desired protein by intracellular or extracellular proteases derived from host cells, a variety of known protease inhibitors, i.e., phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetraacetic acid (EDTA), and/or other commercially available protease inhibitors may be added at appropriate concentrations.

Furthermore, in order to allow accurate folding of the proteins of, the present invention, molecular chaperones such as GroEL/ES, Hsp70/DnaK, Hsp90 and Hsp104/ClpB may be used (for example, such a molecular chaperone may be coexpressed with a protein of the present invention or may be allowed to coexist with a protein of the present invention, for example, by combining them into a fusion protein.) Further examples of techniques for accurate folding of the proteins of the present invention include, but are not limited to, addition of an additive for assisting accurate folding to the medium; and culturing at low temperatures.

Examples of media that can be used to culture the transformants obtained using *Escherichia coli* host cells include LB medium (1% triptone, 0.5% yeast extract, 1% NaCl) and 2xYT medium (1.6% triptone, 1.0% yeast extract, 0.5% NaCl).

Examples of media that can be used to culture the transformants obtained using *Brevibacillus* host cells include TM medium (1% peptone, 0.5% meat extract, 0.2% yeast extract, 1% glucose, pH 7.0) and 2SL medium (4% peptone, 05% yeast extract, 2% glucose, pH 7.2).

Moreover, the proteins of the present invention are accumulated in the cultured cells (including the pen plasmic space thereof) or in the culture fluids (extracellularly) by aerobically culturing the cells at a temperature of 15° C. to 42° C., preferably 20° C. to 37° C., for several hours to several days under aeration and stirring conditions, and then recovered. Optionally, the cells may be cultured anaerobically by blocking the air supply.

In the case where a recombinant protein is produced and secreted, the produced recombinant protein can be recovered, after culture, by separating the cultured cells from the supernatant containing the secreted protein by a common separation method such as centrifugation or filtration.

Also, in the case where the protein is accumulated in the cultured cells (including the periplasmic space thereof), the protein produced and accumulated in the cells can be recovered, for example, by collecting the cells from the culture fluid by centrifugation, filtration or the like, and then disrupting the cells by sonication, French press or the like, and/or adding an agent for making the protein soluble, such as a surfactant.

Purification of the proteins of the present invention may be accomplished by one or an appropriate combination of techniques such as affinity chromatography, cation or anion exchange chromatography and gel filtration chromatography.

Whether a purified product is a desired protein may be confirmed by common methods, such as SOS polyacrylamide gel electrophoresis, N-terminal amino acid sequencing, or Western blot analysis.

EXAMPLES

The following description is offered to illustrate the present invention in more detail by reference to examples, but the scope of the present invention is not limited to these examples. Proteins obtained in the examples are each represented by "an alphabet indicating a domain—an introduced mutation (wild for the wild type)".

For example, the wild-type C domain of Protein A is represented by "C-wild", and a C domain variant containing the G29E mutation is represented by "C-G29E". Variants containing two mutations together are represented by indicating the two mutations together with a slash.

For example, a C domain variant containing the G29E and S13L mutations is represented by "C-G29E/S13L". For proteins containing a plurality of single domains connected together, a period (.) and the number of connected domains followed by "d" are further added.

For example, a protein consisting of five connected C domain variants containing the G29A and S13L mutations is represented by "C-G29A/S13L.5d".

Example 1

Preparation of Ligand Expression Plasmid

Affinity ligands were designed based on a C domain variant of Protein A (C-K04R/K07R/G29A/S33R/K35R/K42R/K49Q/K50R.1d, SEQ ID NO:7) in which all Lys residues, except Lys-58 at the C terminal, have been substituted with other amino acid residues. The following affinity ligands were used in this example: C-K04R/K07R/G29A/S33R/K35R/K42R/K49Q/K50R.5d (SEQ ID NO:8) in which five of such domains were connected; C-K04R/K07R/G29A/S33R/K35R/K42R/K490/K50R.4d (SEQ ID NO: 9) in which four of such domains were connected; and C-K04R/K07R/G29A/S33R/K35R/K42R/K49Q/K50R(C-terminal K58R).4d (SEQ ID NO:10) that is a single residue variant of SEQ ID NO:9 in which Lys-58 of the most C-terminal domain, among the connected four domains, was substituted with Arg. Expression plasmids for these ligands were prepared as described below.

The entire DNA sequence (SEQ ID NO:11) encoding C-K04R/K07R/G29A/S33R/K35R/K42R/K49Q/K50R.5d and containing the NcoI recognition site at the 5 terminal and the XbaI recognition site at the 3' terminal was synthesized by an external institution (Eurogentec). It was subcloned into the expression plasmid (pUC57), which was then digested with restriction enzymes (NcoI and XbaI: both available from Takara Bio, Inc.) to obtain a DNA encoding C-K04R/K07R/G29A/S33R/K35R/K42R/K49Q/K50R.5d, which was then ligated to a *Brevibacillus* expression vector pNK3260', whereby an expression plasmid containing the DNA encoding the amino acid sequence of SEQ ID NO:8 inserted into the *Brevibacillus* expression vector pNK3260' was prepared.

PCR was also performed using the vector pNK3260' containing the DNA encoding the amino acid sequence of SEQ ID NO:8 as a template and oligonucleotide primers of SEQ ID NOs:12 and 13 (synthesized by an external institution (Sigma-Aldrich Japan)) to synthesize a DNA (SEQ ID NO:14, including the NcoI/XbaI sites) encoding C-K04R/K07R/G29A/S33R/K35R/K42R/K49Q/K50R.4d, and the DNA was digested with restriction enzymes (NcoI and XbaI), and then ligated to pNK3260'.

Likewise, PCR was performed using the vector pNK3260' containing the DNA encoding the amino acid sequence of SEQ ID NO:8 as a template and oligonucleotide primers of SEQ ID NOs:12 and 15 to synthesize a DNA (SEQ ID NO: 16, including NcoI/XbaI sites) encoding C-K04R/K07R/G29A/S33R/K35R/K42R/K49Q/K50R(C-terminal K58R).4d), and the DNA was digested with restriction enzymes (NcoI and XbaI), and then ligated to pNK3260'.

The PCR using the DNA polymerase Blend Taq (TOYOBO CO., LTD.) and the ligation using Ligation high ver.2 (TOYOBO CO., LTD.) were carried out in accordance with the protocols of TOYOBO CO., LTD, The digestion using the restriction enzymes was carried out in accordance with the protocol of Takara Bio, Inc.

Finally, expression plasmids respectively containing DNAs encoding the amino acid sequences of SEQ ID NOs:8 to 10 inserted into the *Brevibacillus* expression vector pNK3260' were prepared.

The vector NK3260' is a vector obtained by mutating a known *Brevibacillus* expression vector (WO 06/004067) to allow a DNA encoding a protein desired to be expressed to be inserted into the NcoI/XbaI site.

Additionally, based on a C domain variant of Protein A (C-K04R/K07R/G29A/S33L/K35R/K42R/K49R/K50R.1d, SEQ ID NO: 17) that contains some different mutations from those described above, an expression plasmid for C-K04R/K07R/G29A/S33L/K35R/K42R/K49R/K50R.3d (SEQ ID NO:18) it which three of such domains were connected was prepared in the same manner. The entire DNA sequence encoding the amino acid sequence of SEQ ID NO:18 was synthesized by an external institution (Eurogentec) as above. The DNA sequence of the coding region including the NcoI/XbaI sites is shown as SEQ ID NO:19.

Example 2

Expression and Purification of Ligand

*Brevibacillus choshinensis* FY-1 was transformed with the expression plasmids prepared in Example 1. The transformation was carried out by a known electroporation method ("Biosci. Biotech. Biochem.", 1997, Vol. 61, pp. 202-203). The *Brevibacillus choshinensis* FY-1 is a Phe and Tyr auxotroph obtained by mutating *Brevibacillus choshinensis* HPD31-OK (JP H06-296485 A).

The recombinant strains of *Brevibacillus choshinensis* FY-1 were individually cultured with shaking at 30° C. for 3 days in 5 mL of 3YC medium (3% polypeptone, 0.2% yeast extract, 3% glucose, 0.01% magnesium sulfate, 0.001% iron sulfate, 0.001% manganese chloride, 0.0001% zinc chloride) containing 60 μg/mL neomycin.

The cultures were centrifuged to remove cells, and the obtained culture supernatants were subjected to cation exchange chromatography using an SP Fast Flow column (GE Healthcare, Japan) to purify (partially purify) the desired proteins. Specifically, sodium acetate was added to the culture supernatants to a final concentration of 50 mM, and hydrochloric acid was also added to the culture supernatants to adjust the pH to 4.0. Then, the culture supernatants were individually applied to an SP Fast Flow column equilibrated with cation exchange buffer A (50 mM $CH_3COOH$—$CH_3COONa$, pH 4.0). After washing with cation exchange buffer A, the desired proteins were eluted and separated in the process of salt gradient elution using cation exchange buffer A and cation exchange buffer B (50 mM $CH_3COOH$—$CH_3COONa$, 1 M NaCl, pH 4.0).

Next, the desired proteins were purified by an anion exchange chromatography using HiTrap Q column (GE Healthcare Bio-Sciences). Specifically, the separated desired protein solutions were individually dialyzed with ultrapure water, and applied to a HiTrap Q column equilibrated with anion exchange buffer A (50 mM Tris-HCl, pH 8.0). After washing with anion exchange buffer A, the desired proteins were eluted and separated in the process of salt gradient elution using anion exchange buffer A and anion exchange buffer B (50 mM Tris-HCl, 1 M NaCl, pH 8.0).

The separated desired protein solutions were dialyzed with ultrapure water, and the dialyzed solutions were used as final purified samples. All the protein purification processes by column chromatography were carried out using an AKTAprime plus system (GE Healthcare Bio-Sciences).

Example 3

Analysis for Affinity of Ligand for Human Immunoglobulin

The ligands obtained in Example 2 were analyzed for affinity for an immunoglobulin with a Biacore 3000 biosensor (GE Healthcare Bio-Sciences) based on surface plasmon resonance. A human immunoglobulin G preparation (hereinafter referred to as human IgG) separated from human plasma was immobilized on a sensor chip, and the ligands obtained in Example 2 were individually flowed over the chip to detect interactions between them.

The immobilization of the human IgG on the sensor chip CM5 was accomplished by amine coupling using N-hydroxysuccinimide (NHS) and N-ethyl-N'-(3-dimethylaminopropyl)carbodiimide hydrochloride (EDC), and ethanolamine was used for blocking (the sensor chip and the immobilization reagents are all available from GE Healthcare Bio-Sciences).

Gammagard (Baxter), which is a commercially available human IgG, was diluted in an immobilization buffer (10 mM $CH_3COOH$—$CH_3COONa$, pH 4.5) to a final ligand concentration of about 50 μg/ml, and the human IgG was immobilized on the sensor chip in accordance with the protocol attached to the Biacore 3000. A reference cell to be used as a negative control was also prepared by immobilizing ethanolamine in a separate flow cell on the chip after activation by EDC/NHS.

The ligand solutions were each diluted to concentrations of 16, 32, 64, and 128 nM using a running buffer (20 mM $NaH_2PO_4$—$Na_2HPO_4$, 150 mM NaCl, 0.005% P-20, pH 7.4), and such ligand solutions were individually injected into the sensor chip at a flow rate of 40 μL/min for 2.5 minutes. Sequential binding response sensorgrams measured at 25° C. were recorded during injection (binding phase, 2.5 minutes) and after injection (dissociation phase, 2.5 minutes). After each recording, the sensor chip was regenerated by sequentially injecting 0.1 M Gly (pH 2.5) and 20 mM NaOH for 0.5 seconds each.

This process was performed to remove the injected protein remaining on the sensor chip, and confirmed to substantially completely restore the binding activity of the immobilized human TgG. Affinity constants of the ligands for the human IgG ($N_A = k_{on}/k_{off}$) were calculated by fitting the obtained sensorgrams (the sensorgrams obtained by subtracting the binding response sensorgram of the reference cell) to a 1:1 binding model using a BIA evaluation software attached to the system.

As seen in Table 1, the affinity constants $K_A$ ($M^{-1}$) of the multi-domain type C domain variants for the human IgG were in the order of $10^9$. These were comparable with, for example, that of a known five-domain type ligand C-G29A/S33E.5d (Comparative Example 1). The techniques of the present invention are for improving the binding "capacity" of a target molecule when the ligands are immobilised, and it is important for the ligand molecules to achieve substantially the same binding "ability" to a target molecule. Accordingly, the data are considered to validate the present invention.

TABLE 1

| Multi-domain type C domain variant | $K_A$ (×$10^9$ $M^{-1}$) |
|---|---|
| *[1]C-G29A/S33E.5d | 6.3 |
| C-K04R/K07R/G29A/S33R/K35R/K42R/K49Q/K50R.5d | 1.5 |
| C-K04R/K07R/G29A/S33R/K35R/K42R/K49Q/K50R.4d | 1.0 |
| C-K04R/K07R/G29A/S33R/K35R/K42R/K49Q/K50R/(C-terminal K58R).4d | 1.1 |
| C-K04R/K07E/G29A/S33L/K35R/K42R/K49R/K50R.3d | 2.1 |

The variant *[1] is the protein obtained in Comparative Example 1.

Example 4

Preparation of Prototype Affinity Separation Matrix with Ligand Immobilized on Carrier Affinity separation matrices were prepared by immobilizing the ligands obtained in Example 2 on a commercially available coupling column for ligand immobilization using an amino group as a functional group for coupling.

As a water-insoluble base material, a commercially available 1-mL prepacked column "Hitrap NHS activated HP" (GE Healthcare Bio-Sciences) was used. This column was made of a cross-linked agarose-based material into which an active group for immobilizing a proteinic ligand via an amino group as a functional group for coupling had been introduced. Thus, the ligands were individually immobilized in accordance with the product manual of the column. The operation of flowing 2 mL of 1 mM HCl cooled in an ice bath at a flow rate of 1 mL/min was repeated three times to remove isopropanol in the column.

Immediately, each of dilutions of the ligands in a coupling buffer (0.2 M $NaHCO_3$, 0.5 M NaCl, pH 8.3) was applied to the column at the same flow rate in an amount of 1 mL. The top and bottom of each column were sealed, and the columns were then left at rest at 25° C. for 30 minutes. In this manner, the obtained ligands were immobilized on the columns.

Thereafter, the columns were opened, and 3 mL of the coupling buffer was flowed through each column at the same flow rate to collect unreacted ligand. Then, the operation of flowing 2 mL of a blocking buffer (0.5 M ethanolamine, 0.5 M NaCl, pH 8.3) was repeated three times, and the operation of flowing 2 mL of a washing buffer (0.1 M acetate, 0.5 M NaCl, pH 4.0) was also repeated three times.

The series of operations of flowing the blocking buffer and of flowing the washing buffer were alternately repeated three times. Finally, 0.2 mL of a standard buffer (20 mM $NaH_2PO_4$—$Na_2HPO_4$, 150 mM NaCl, pH 7.4) was flowed through each column, whereby the preparation of each affinity separation column was completed.

NHS, which was replaced in the immobilization reaction, absorbs at 280 nm. NHS was removed using a HiTrap Desalting 5 mL column (GE Healthcare Bio-Sciences), and the absorbance of unreacted ligand alone at 280 nm ($Abs_{280}$) was measured to calculate the immobilization yield. The use of the HiTrap Desalting column enables components having a molecular weight of not less than 5,000 (the ligands in this experiment) and components having a molecular weight of not more than 1,000 (replaced. NHS) to be separated from each other.

An amount of 500 μL of unreacted ligand was passed through the HiTrap Desalting 5 mL column, and 1 mL of the coupling buffer was added, followed by further adding 1.5 mL of the coupling buffer. At this time, 1.5 mL of the eluate was recovered and measured for absorbance at 280 nm. The concentration was calculated using the calculation formula (when the $Abs_{280}$ is 0.484, the concentration is 1 mg/mL) obtained previously from studies by HPLC or the biuret test.

Table 2 shows the concentration (loading) of the ligand dilutions, the amount of ligand immobilized, and the immobilization yield.

For example, C-K04R/K07R/G29A/S33L/K35R/K42R/K49R/K50R.3d (SEQ ID NO:18) is mostly immobilized on a matrix in a manner shown in FIG. 1(4) using the side chain amino groups of the lysine residues which are respectively present in the two interdomain linker regions and the C terminal in the ligand. Although there is a possibility that the ligand could be immobilized via the amino group of the N-terminal amino acid residue in the ligand, this possibility is low for the reason of reactivity. Even when only a small percentage of the ligand is immobilized at the N-terminal amino acid residue, the ligand is immobilized in a manner shown in FIG. 1(6). Thus, this case presumably provides the same effects as those provided by the present invention. Although the numbers of domains are different, the five-domain type C-K04R/K07R/G29A/S33R/K35R/K42R/K49Q/K50R.5d (SEQ ID NO:8) and the four-domain type C-K04R/K07R/G29A/S33R/K35R/K42R/K49Q/K50R.4d (SEQ ID NO:9) are also immobilized in the same manner shown in FIG. 1(4). Moreover, C-K04R/K07R/G29A/S33R/K35R/K42R/K49Q/K50R(C-terminal K58R).4d (SEQ ID NO: 10) that differs from SEQ ID NO: 9 only by removal of the C-terminal Lys is immobilized in a manner shown in FIG. 1(7).

TABLE 2

| Prototype ID | Number of Lys residues in ligand [residue] | Ligand loading [mg/mL] | Amount of ligand immobilized [mg/mL-gel] | Immobilization yield [%] |
|---|---|---|---|---|
| Prototype 1 | 5 | 7.0 | 6.4 | 91 |
|  | 5 | 11.9 | 9.5 | 80 |
|  | 5 | 17.3 | 12.5 | 73 |
| Prototype 2 | 4 | 7.2 | 6.8 | 95 |
|  | 4 | 17.8 | 14.1 | 79 |
| Prototype 3 | 3 | 7.3 | 6.9 | 95 |
|  | 3 | 17.5 | 13.5 | 77 |

TABLE 2-continued

| Prototype ID | Number of Lys residues in ligand [residue] | Ligand loading [mg/mL] | Amount of ligand immobilized [mg/mL-gel] | Immobilization yield [%] |
|---|---|---|---|---|
| Prototype 4 | 3 | 6.0 | 4.8 | 81 |
|  | 3 | 14 | 9.4 | 68 |

Prototype 1: C-K04R/K07R/G29A/S33R/K35R/K42R/K49Q/K50R.5d
Prototype 2: C-K04R/K07R/G29A/S33R/K35R/K42R/K49Q/K50R.4d
Prototype 3: C-K04R/K07R/G29A/S33R/K35R/K42R/K49Q/K50R/
(C-terminal K58R).4d
Prototype 4: C-K04R/K07R/G29A/S33L/K35R/K42R/K49R/K50R.3d Example 5

Evaluation of Human IgG Binding Capacity of Prototype Affinity Separation Matrix In order to evaluate the human IgG binding capacity of the prototype affinity separation matrices, the prototype affinity separation matrices were measured for antibody dBC by an affinity chromatography experiment.

Gamma globulin (Nichiyaku) was diluted with a standard buffer (100 mM $NaH_2PO_4$—$Na_2HPO_4$, 138 mM NaCl, 2.7 mM KCl, pH 7.4) to 1/150 to prepare a 1 mg/ml, solution, which was used as a human IgG.

Moreover, the $Abs_{280}$ while this solution was being passed 100% through a cell of an AKTAexplorer 100 chromatography system (GE Healthcare Bio-Sciences) (100% $Abs_{280}$) was measured in advance. In a series of operations, it should be noted that 1 mL was regarded as 1 CV because the HiTrap NHS Activated HP (1 mL) had a size of φ 0.7×2.5 cm (0.96 mL).

The prototype affinity separation matrices were each connected to the AKTAexplorer 100 chromatography system, and 5 CV of a standard buffer (100 mM $NaH_2PO_4$—$Na_2HPO_4$, 138 mM NaCl, 2.7 mM KCl, pH 7.4) was flowed at 1.0 mL/min to equilibrate the column. Then, the human IgG solution was flowed at 0.2 mL/min (31 cm/h) until the monitored absorbance exceeded 5% of the 100% $Abs_{280}$. Thereafter, 5 CV of the standard buffer was flowed at 1.0 mL/min, and then 3 CV of an elution buffer (35 mM acetate, pH 3.5) was flowed to elute the human IgG. The total amount of the human IgG flowed until the monitored absorbance exceeded 5% of the 100% $Abs_{280}$ was defined as antibody dBC (5% antibody dBC).

The evaluation results of the prototype five-domain type affinity separation matrix are shown in Table 3.

TABLE 3

| Prototype ID | Number of Lys residues in ligand [residue] | Antibody affinity constant $K_A$ [×10$^9$ M$^{-1}$] | Amount of ligand immobilized [mg/mL-gel] | 5% antibody dBC [mg/mL-gel] |
|---|---|---|---|---|
| Comparison 1 | 35 | 6.3 | 5.7 | 38.3 |
|  | 35 | 6.3 | 8.8 | 50.3 |
|  | 35 | 6.3 | 10.9 | 54.4 |
| Prototype 1 | 5 | 1.5 | 6.4 | 45.8 |
|  | 5 | 1.5 | 9.5 | 55.3 |
|  | 5 | 1.5 | 12.5 | 61.3 |

Figure 3:
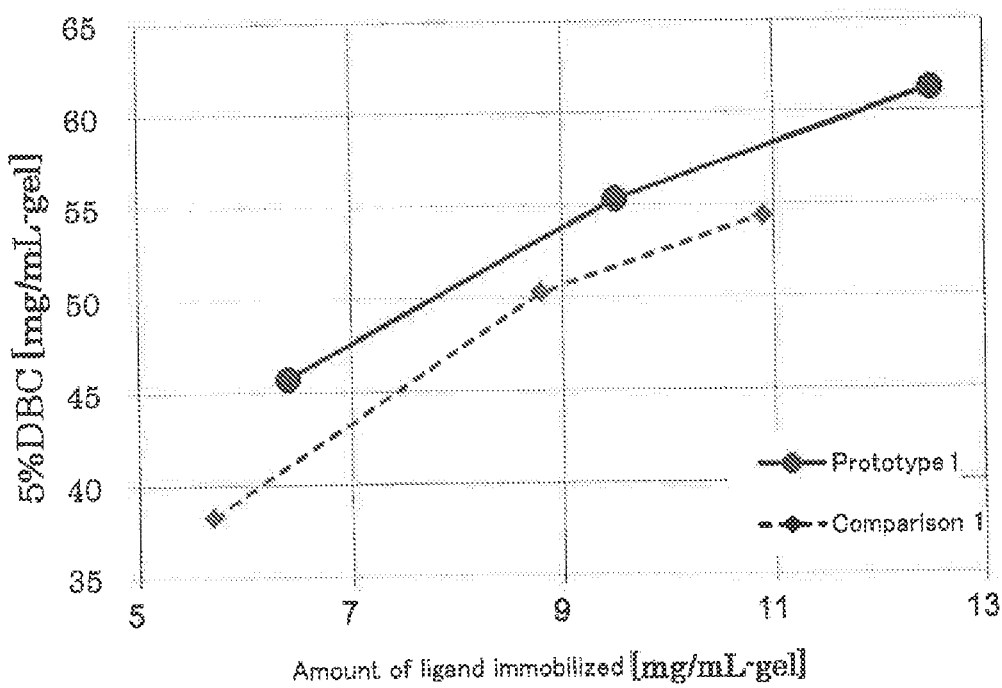
FIG. 3 is a graph plotting the relationship between the amount of ligand immobilized and the antibody binding capacity of affinity separation matrices that contain the same ligand immobilized in a different manner with each other.

Comparison 1: C-G29A/S33E.5d
Prototype 1: C-K04R/K07R/G29A/S33R/K35R/K42R/K49Q/K50R.5d FIG. 3 shows the results of Table 3 plotted on a graph where the horizontal axis represents the immobilized amount, and the vertical axis represents the antibody dBC.

It is demonstrated that the affinity separation matrix obtained according to the present invention had a significantly higher antibody dBC than the affinity separation matrix of Comparative Example 1 at substantially the same amount of ligand immobilized. The trends of the plots of FIG. 3 where the antibody dBCs of the two different ligands are plotted for comparison at three different immobilized amounts suggest that the affinity separation matrix according to the present invention in which the ligand was immobilized on a carrier, in a manner shown in FIG. 1(4) tended to have a clearly higher antibody dBC than that in which the ligand was immobilized in a manner shown in FIG. 1(1).

Table 4 shows the evaluation results of the prototype four-domain type affinity separation matrices.

TABLE 4

| Prototype ID | Number of Lys residues in ligand [residue] | Antibody affinity constant $K_A$ [×10$^9$ M$^{-1}$] | Amount of ligand immobilized [mg/mL-gel] | 5% antibody dBC [mg/mL-gel] |
|---|---|---|---|---|
| Prototype 2 | 4 | 1.0 | 6.8 | 42.6 |
|  | 4 | 1.0 | 14.1 | 62.1 |
| Prototype 3 | 3 | 1.1 | 6.9 | 41.8 |
|  | 3 | 1.1 | 13.5 | 62.1 |

Prototype 2: C-K04R/K07R/G29A/S33R/K35R/K42R/K49Q/K50R.4d
Prototype 3: C-K04R/K07R/G29A/S33R/K35R/K42R/K49Q/K50R/
(C-terminal K58R).4d The results indicate that the affinity separation matrix obtained according to the present invention in which the ligand was immobilized, for example, in a manner shown in FIG. 1(7) had a comparable antibody dBC to that of the affinity separation matrix in which the ligand was immobilized in a manner shown in FIG. 1(4).

In other words, all the forms shown in FIG. 1(4)-(7) are expected to provide the antibody dBC improving effect described above, and theoretically, all the forms of (4) to (15) are expected to provide the same effect. It was also found that similar effects are obtained regardless of changes in the number of domains.

Table 5 shows the evaluation results of the prototype three-domain type affinity separation matrix.

TABLE 5

| Prototype ID | Number of Lys residues in ligand [residue] | Antibody affinity constant $K_A$ [×10$^9$ M$^{-1}$] | Amount of ligand immobilized [mg/mL-gel] | 5% antibody dBC [mg/mL-gel] |
|---|---|---|---|---|
| Comparison 2 | 1 | 2.2 | 5.1 | 49.1 |
|  | 1 | 2.2 | 9.0 | 66.2 |
| Prototype 4 | 3 | 2.1 | 4.8 | 56.5 |
|  | 3 | 2.1 | 9.4 | 73.4 |

Comparison 2: C-K04R/K07R/G29A/S33L/K35R/K42R/K49R/K50R/
(K58R except for C-terminal).3d
Prototype 4: C-K04R/K07R/G29A/S33L/K35R/K42R/K49R/K50R.3d The affinity separation matrix obtained according to the present invention had a significantly higher antibody dBC than the affinity separation matrix of Comparative Example 2 at substantially the same amount of ligand immobilized. These data suggest that the affinity separation matrices obtained according to the present invention have a significantly higher antibody dBC than affinity separation matrices in which the ligand is immobilized in a manner shown in FIG. 1(2).

It was also found that similar effects are obtained regardless of changes in the number of domains and the type of sequence as long as the domains have the antibody binding ability.

Comparative Example 1

C-G29A/S33E.5d

A five-domain ligand intended to be immobilized on a carrier in a manner shown in FIG. 1(1) was obtained as a reference ligand, and an affinity separation matrix in which the ligand was immobilized was prepared.

An expression plasmid for C-G29A/S33E.5d (SEQ ID NO:20) was prepared in accordance with the disclosure of the published patent application (WO 2010/110288). The sequence of the coding DNA is shown as SEQ ID NO:21. The expression plasmid can be easily prepared, for example, by synthesizing the entire DNA sequence and introducing the DNA into a commercially available *Brevibacillus* expression plasmid (for example, pNCMO2 available from Takara Bio, Inc.).

Expression and purification of the ligand were carried out as described in Example 2. The obtained ligand was measured for affinity for human IgG in the same manner as in Example 3. The results are shown in Table 1. An affinity separation matrix in which the obtained ligand was immobilized was prepared as described in Example 4, and then measured for antibody dBC as described in Example 5. The results are shown in Table 3 and FIG. 3.

Comparative Example 2

C-K04R/K07R/G29A/S33L/K35R/K42/K49R/K50R/(K58R Except for C-Terminal).3d

A three-domain ligand intended to be immobilized on a carrier in a manner shown in FIG. 1(2) was obtained as a reference ligand, and an affinity separation matrix in which the ligand was immobilized was prepared.

The entire DNA sequence (SEQ ID NO:23) encoding C-K04R/K07R/G29A/S33L/K35R/K42R/K49R/K50R/(K58R except for C-terminal) 3d (SEQ ID NO:22) and containing the NcoI recognition site at the 5' terminal and the XbaI recognition site at the 3' terminal was synthesized by an external institution (Eurogentec).

This ligand is intended to be immobilized on a carrier only via Lys-58 of the third domain (at the C terminal of the ligand sequence). An expression plasmid containing its DNA was prepared as described in Example 1, and expression and purification of the ligand were carried out as described in Example 2, The obtained ligand was measured for affinity for human IgG as described in Example 3, and the affinity constant ($K_A$) is shown in Table 5. An affinity separation matrix in which the obtained ligand was immobilized on a carrier was also prepared as described in Example 4, and the antibody dBC measured as described in Example 5 is also shown in Table 5

Example 6

Preparation of Cellulose Beads for Matrix (1) Preparation of Cellulose Dispersion B A mixture of 76 g of Japanese Pharmacopoeia cellulose PH-F20JP (Asahi Kasei Chemicals Corp.; median particle size: 21 μm), and 800 g of distilled water was stirred while adjusting the temperature to 4° C. To the mixture was then added 400 g of alkaline aqueous solution A having a temperature adjusted to 4° C. while maintaining stirring at the adjusted temperature, followed by stirring for 30 minutes.

(2) Preparation of Porous Cellulose Beads

An amount of 1276 g of cellulose dispersion. B having a temperature adjusted to 4° C., 7801 g of o-dichlorobenzene having a temperature adjusted to 4° C. and 78 g of sorbitan monooleate (span 80 equivalent) having a temperature adjusted to 4° C. were mixed, and the mixture was stirred in a stainless steel container equipped with two disc turbine impellers (Rushton turbine) at 460 rpm (Pv value: 5.0 $kW/m^3$) at 4° C. for 15 minutes to prepare an emulsion. To the emulsion 592 g of methanol having a temperature adjusted to 0.4° C. was added as a coagulating solvent while maintaining stirring at the adjusted temperature. The time required for adding the coagulating solvent was 5 seconds. Then, the mixture was stirred while maintaining the stirring rate and the adjusted temperature for 30 minutes. After pressure filtration, washing was carried out using as a washing solution 3000 g of methanol and subsequently 3000 g of water to provide porous cellulose beads. The obtained porous cellulose beads were wet-classified using sieves of 38 μm and 90 μm.

(3) Crosslinking

Distilled water was added to 20 parts by volume of the above porous cellulose beads to give a volume of 30 parts by volume, and the mixture was transferred to a reaction vessel. Thereto was added 2.3 parts by weight of DENACOL EX-314 (available from Nagase ChemteX Corporation) containing glycerol polyglycidyl ether as a crosslinking agent, and the mixture was continuously stirred while adjusting the temperature to 40° C. After the temperature was adjusted at 40° C., the mixture was stirred for 30 minutes. Next, 7.1 parts by volume of a 2 N NaOH aqueous solution was prepared, and a quarter of the solution was added every one hour. During the addition, the temperature was maintained at 40° C. and the stirring was also continued. After the last quarter was added, the mixture was stirred for one hour at the same temperature. After completion of the reaction, the beads were washed with distilled water in an amount of at least 20 times the volume of the beads with suction filtration. In this manner, one-time cross-linked beads were prepared.

The obtained one-time cross-linked beads were transferred to a vessel. Distilled water was added thereto to a total volume of 10 times the volume of the cross-linked porous cellulose, beads. The mixture was heated at 120° C. for one hour using an autoclave. After the mixture was allowed to cool down to room temperature, the beads were washed with RO water in an amount of at least 5 times the volume of the beads, to prepare autoclaved one-time cross-linked beads in which the epoxy group was converted to a glyceryl group.

Next, distilled water was added to 20 parts by volume of the autoclaved one-time cross-linked beads to give a volume of 30 parts by volume. The mixture was transferred to a reaction vessel. Thereto was added 2.3 parts by weight of DENACOL EX-314 containing glycerol polyglycidyl ether as a crosslinking agent, and the mixture was continuously stirred while adjusting the temperature to 40° C. After the temperature was adjusted at 40° C., the mixture was stirred for 30 minutes. Next, 7.1 parts by volume of a 2 N NaOH aqueous solution was prepared, and a quarter of the solution was added every one hour. During the addition, the temperature was maintained at 40° C. and the stirring was also continued. After the last quarter was added, the mixture was stirred for one hour at the same temperature. After completion of the reaction, the beads were washed with distilled water in an amount of at least 20 times the volume of the beads with suction filtration. In this manner, two-time cross-linked beads were prepared.

The obtained two-time cross-linked beads were transferred to a vessel. Distilled water was added thereto to a total volume of 10 times the volume of the cross-linked porous cellulose beads. The mixture was heated at 120° C. for 60 minutes using an autoclave. After the mixture was allowed to cool down to room temperature, the beads were washed with distilled water in an amount of at least 5 times the volume of the beads, to prepare autoclaved two-time cross-linked beads.

Example 7

Exemplary Prototype Affinity Separation Matrix with Ligand Immobilized on Cellulose Beads To 3.5 mL of the cross-linked porous cellulose beads prepared in Example 6 in a centrifuge tube was added RO water to a total amount of 6 mL. The tube at 25° C. was attached onto the mix rotor MR-3 (AS ONE Corporation), followed by stirring. Subsequently, 2.0 mL of a 11.16 mg/mL sodium periodate aqueous solution prepared by dissolving sodium periodate (Wako Pure Chemical Industries, Ltd.) in RO water was added and the mixture was stirred at 25° C. for one hour. After the reaction, the beads were washed with RO water on a glass filter (11GP100, available from SIBATA SCIENTIFIC TECHNOLOGY LTD.) until the electric conductivity of the filtrate reached 1 μS/cm or lower, to prepare formyl group-containing cross-linked porous cellulose beads. The electric conductivity of the washing filtrate was measured with an ECTester 10 Pure+ conductivity meter (EUTECH INSTRUMENTS).

An amount of 3.5 mL of the obtained formyl group-containing cross-linked porous cellulose beads was substituted on a glass filter (11GP100, available from SIBATA SCIENTIFIC TECHNOLOGY LTD.) with a 0.6 M citric acid buffer (pH 12, prepared using trisodium citrate dihydrate (Wako Pure Chemical Industries, Ltd.), sodium hydroxide and RO water). The substituted formyl group-containing cross-linked porous cellulose beads were transferred into a centrifuge tube using the citric acid buffer, and the fluid volume was adjusted to a total volume of 7.5 mL. To this tube was added the ligand solution obtained in Example 2, and the mixture was reacted at 6° C. for 23 hours with stirring using the mix rotor MR-3.

Then, the reaction solution (reaction solution 1) was recovered, and substituted with a 0.1 M sodium citrate aqueous solution (pH 8, prepared using trisodium citrate dihydrate (Wako Pure. Chemical Industries, Ltd.) and RO water), and the resulting mixture was stirred with the mix rotor MR-3 at 6° C. for 4 hours. Subsequently, 1.93 mL of a 5.5% by weight dimethylamine borane aqueous solution (prepared using dimethylamine borane (Wako Pure Chemical Industries, Ltd.) and RO water) was added and the mixture was stirred at 6° C. for one hour. Then, the reaction temperature was increased to 25° C., and the mixture was reacted at 25° C. for 18 hours with stirring using the mix rotor MR-3. After the reaction, the reaction solution (reaction solution 2) was recovered. The reaction solutions 1 and 2 were measured for UV absorption maximum near 278 nm, and the measured amounts were subtracted from the respective ligand loadings to calculate the amount of ligand immobilized. Table 6 shows the ligand loading, the amount of ligand immobilized and the immobilization yield.

TABLE 6

| Prototype ID | Number of Lys residues in ligand [residue] | Ligand loading [mg/mL] | Amount of ligand immobilized [mg/mL-gel] | Immobilization yield [%] |
|---|---|---|---|---|
| Prototype 1(C) | 5 | 15.0 | 11.0 | 73 |
| Comparison 1(C) | 35 | 13.0 | 11.6 | 89 |

((C) in Prototype ID indicates the use of a cellulose-based carrier.)
Prototype 1: C-K04R/K07R/G29A/S33R/K35R/K42R/K49Q/K50R.5d
Comparison 1: C-G29A/S33E.5d The beads obtained after the reaction were washed on a glass filter 11GP100 (SIBATA SCIENTIFIC TECHNOLOGY LTD.) with RO water in an amount of 3 times the volume of the beads. Next, thereto was added 3 times the volume of 0.1 N citric acid monohydrate (prepared using citric acid monohydrate (Kanto Chemical Co., Inc.) and RO water) so that the 0.1 N citric acid monohydrate was added to the beads to a total amount of 30 mL or more. The mixture was transferred to a centrifuge tube, and acid washed at 25° C. for 30 minutes with stirring. After the acid washing, the beads were washed on a glass filter 11GP100 with RO water in an amount of 3 times the volume of the beads, and then combined with 3 times the volume of a 0.05 M sodium hydroxide +1 M sodium sulfate aqueous solution. Subsequently, the beads were combined with a 0.05 M sodium hydroxide +1 M sodium sulfate aqueous solution to a total amount of 30 mL or more, and the mixture was transferred to a centrifuge tube, and alkali washed at room temperature for 30 minutes with stirring.

After the alkali washing, the beads were washed on a glass filter (11GP100 available from SIBATA SCIENTIFIC TECHNOLOGY LTD.) with RO water in an amount of 20 times the volume of the beads. Then, a 0.1 N sodium citrate aqueous solution was added in an amount of 3 times the volume of the beads. After the filtrate was confirmed to be neutral, the beads were washed with RO water until the electric conductivity of the washing filtrate reached 1 μS/cm or lower, to obtain a desired affinity separation matrix. The electric conductivity of the washing filtrate was measured with an ECTester 10 Pure+ conductivity meter.

Example 8

Evaluation of Human IgG Binding Capacity of Cellulose-Based Affinity Separation Matrix In order to evaluate the human IgG binding capacity of the prototype affinity separation matrix prepared in Example 7, the prototype affinity separation matrix was measured for antibody dBC by an affinity chromatography experiment.

AKTAexplorer 100 (GE Healthcare Bio-Sciences) was used as a chromatography system, and a 22 μm mesh was attached to a column (diameter 0.5 cm, height 15 cm). The prototype affinity separation matrix (3 mL) was put in each column, and a 20% ethanol aqueous solution was passed therethrough at a linear velocity of 450 cm/h for one hour. Thus, a prototype affinity separation matrix-filled column was obtained. In the following procedure, the dynamic binding capacity to IgG was measured in the same manner as in Example 5.

Table 7 shows the evaluation results of the prototype cellulose-based affinity separation matrix.

TABLE 7

| Prototype ID | Number of Lys residues in ligand [residue] | Antibody affinity constant $K_A$ [$\times 10^9 M^{-1}$] | Amount of ligand immobilized [mg/mL-gel] | 5% antibody dBC [mg/mL-gel] |
| --- | --- | --- | --- | --- |
| Prototype 1(C) | 5 | 1.5 | 11.0 | 46.1 |
| Comparison 1(C) | 35 | 6.3 | 11.6 | 36.8 |

((C) in Prototype ID indicates the use of a cellulose-based carrier.)
Prototype 1: C-K04R/K07R/G29A/S33R/K35R/K42R/K49Q/K50R.5d
Comparison 1: C-G29A/S33E.5d It was demonstrated that the cellulose-based affinity separation matrix obtained according to the present invention had a significantly higher antibody dBC than the affinity separation matrix of Comparative Example 3 at substantially the same amount of ligand immobilized. This suggests that affinity separation matrices obtained according to the present invention produce a similar antibody dBC improving effect regardless of the type of base material of the matrices.

Example 9

Measurement of Ligand Leakage

The affinity separation matrix obtained in Example 4 was used to evaluate ligand leakage. Human IgG was added to the matrix and eluted with an acidic solution. Then, the ligand content in the IgG eluate was measured. The chromatography system used was AKTAexplorer 100. A 15 ml collection tube was attached to a fraction collector, and a neutralization solution was put in the eluate collection tube in advance. IgG was eluted and the eluate was collected in the same manner as in Example 5.

The IgG content and ligand (Protein A) content in the eluate were measured to determine the concentration of ligand leaked into the purified IgG (leakage). The amount of leakage was determined by the ELISA method disclosed in the reference (Steindl F. et al., "Journal of Immunological Methods", 2000, Vol. 235, pp. 61-69). Table 8 shows the results for determination of ligand leakage.

TABLE 8

| Prototype ID | Number of Lys residues in ligand [residue] | Amount of ligand immobilized [mg/mL-gel] | Ligand leakage [ppm] |
| --- | --- | --- | --- |
| Prototype 1 | 5 | 9.5 | 43 |
| Comparison 3 | 1 | 9.4 | 225 |

Prototype 1: C-K04R/K07R/G29A/S33R/K35R/K42R/K49Q/K50R.5d
Comparison. 3: C-K04R/K07R/G29A/S33R/K35R/K42R/K49Q/K50R/(K58R except for C-terminal).5d It was demonstrated that the affinity separation matrix obtained according to the present invention in which the ligand was immobilized in a manner shown in FIG. 1(4) exhibited a significantly suppressed ligand leakage as compared to the affinity separation matrix of Comparative Example 4 in which the ligand was immobilized in a manner shown in FIG. 1(2). This suggests that both high antibody dBC and low ligand leakage can be achieved according to the present invention, Comparative Example 3

Affinity Separation Matrix with C-G29A/S33E.5d Immobilized on Cellulose Beads

An affinity separation matrix was obtained by immobilizing C-G29A/S33E.5d obtained in Comparative Example 1 on cellulose beads in a manner described below. A formylated carrier was prepared in the same manner as in Example 7, and 3.5 mL of the obtained formyl group-containing cross-linked porous cellulose beads were substituted on a glass filter (11GP100 available from SIBATA SCIENTIFIC TECHNOLOGY LTD.) with a 0.25 N citric acid buffer (pH 12, prepared using trisodium citrate dihydrate (Wako Pure Chemical Industries, Ltd.), sodium hydroxide and RO water). The substituted formyl group-containing cross-linked porous cellulose beads were transferred into a centrifuge tube using the 0.25 N citric acid buffer (pH 12), and the fluid volume was adjusted to a total volume of 7.5 mL. To this tube was added 0.63 g of the C-G29A/S33E.5d solution (66.7 mg/mL), and the mixture was reacted at 6° C. for 23 hours with stirring using the mix rotor MR-3.

Then, 2.4 M aqueous citric acid (prepared using citric acid monohydrate (Wako Pure Chemical Industries, Ltd.) and RD water) was used to adjust the pH of the reaction solution to 5.0, and the mixture was stirred with the mix rotor MR-3 at 6° C. for 4 hours. Then, the same reduction and washing procedures as in Example 6 were performed. The concentration (loading) of the ligand dilution, the amount of ligand immobilized, and the immobilization yield are also shown in Table 6. The human IgG binding capacity of the affinity separation matrix was measured as described in Example 8. The results are also shown in Table 7.

Comparative Example 4

Affinity Separation Matrix with C-K04R/K07R/G29A/S33R/K35R/K42R/K49Q/K50R/(K58R Except for C-Terminal).5d Immobilized on Agarose-Based Carrier A five-domain ligand intended to be immobilized on a carrier in a manner shown in FIG. 1(2) was obtained as a reference ligand, and an affinity separation matrix in which the ligand was immobilized was prepared.

Based on a C domain variant of Protein. A (C-K04R/K07R/G29A/S33R/K35R/K42R/K49Q/K50R/K58R.1d, SEQ ID NO:24), an expression plasmid for C-K04R/K07R/G29A/S33R/K35R/K42R/K49Q/K50R/(K58 except for C-terminal).5d (SEQ ID NO:25) in which five of such domains were connected, and Lys-58 was substituted with Arg, except for the C-terminal domain, was prepared in the same manner. The entire DNA encoding the amino acid sequence of SEQ ID NO:25 was synthesized by an external institution (Euroqentec) similarly to Example 1. The DNA sequence of the coding region including the NcoI/XbaI sites is shown as SEQ ID NO:26. Expression and purification of C-K04R/K07R/G29A/S33R/K35R/K42R/K49Q/K50R/K58R(K58R except for C-terminal).5d (SEQ ID NO:25) were carried out in the same manner as in Example 2 to obtain a ligand, Ar affinity separation matrix in which this ligand was immobilized was prepared in the same manner as in Example 4. When the concentration (loading) of the ligand dilution used for preparation was 12.1 mg/mL, the amount of ligand immobilized was found to be 9.4 mg/mL-gel, and the immobilization yield was found to be 77%. The ligand leakage from the affinity separation matrix was measured as described in Example 9 The results are also shown in Table 8.

The invention claimed is:

1. A protein, comprising three or more amino acid sequences derived from any domain selected from E, D, A, B, and C domains of Protein A, the amino acid sequences comprising amino acid substitutions for all lysine residues (Lys) in the domains,
   wherein the amino acid sequences are connected to one another through one or more linkers,
   wherein (i) at least two of the linkers contain a lysine residue (Lys) or a cysteine residue (Cys), or
   (ii) at least one of the linkers contains a lysine residue or a cysteine residue, and a region within 4 or less residues from N- or C-terminus of the protein comprises a lysine residue or a cysteine residue,
   at least 90% of the following amino acid residues: Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 (the residue numbers indicated are corresponding residue numbers of the C domain and the positions of the conserved amino acids for any domain selected from E, D, A and B domains are respectively compared to the C domain positions upon alignment with the C domain of any domain selected from E, D, A and B domains) are conserved in any domain selected from E, D, A, B, and C domains in the protein, and
   the amino acid sequences having at least 80% sequence identity to the amino acid sequences of the E, D, A, B, or C domains before the lysine substitutions.

2. The protein according to claim 1, wherein at least one of the linkers contains Lys.

3. The protein according to claim 1, wherein the amino acid sequences before the substitutions are any of the amino acid sequences of SEQ ID NOs:1 to 5 or any of the amino acid sequences of SEQ ID NOs:1 to 5 comprising at least one of the following mutations (1) to (4):
(1) a substitution of Ala, Val, Leu, Ile, Phe, Tyr, Trp, Thr, Ser, Asp, Glu, Arg, His, or Met for an amino acid residue in the domain corresponding to position 29 of the C domain;
(2) a substitution of Leu, Ile, Phe, Tyr, Trp, Thr, Asp, Glu, Asn, Gln, Arg, His, or Met for an amino acid residue in the domain corresponding to position 33 of the C domain;
(3) a substitution of Leu, Ile, Phe, Tyr, Trp, Glu, Arg, His, or Met for an amino acid residue in the domain corresponding to position 36 of the C domain; and
(4) a substitution of Leu, Ile, Phe, Tyr, Trp, Glu, Arg, His, or Met for an amino acid residue in the domain corresponding to position 37 of the C domain.

4. The protein according to claim 1, wherein at least half of all the amino acid substitutions for Lys are substitutions to Arg.

5. The protein according to claim 1, wherein all the amino acid substitutions for Lys are substitutions to Arg.

6. The protein according to claim 1, comprising Lys or Cys at at least one terminal region thereof.

7. The protein according to claim 1, comprising Lys at at least one terminal region thereof.

8. A method for producing the protein according to claim 1, comprising either using a cell-free protein synthesis system comprising a DNA encoding said protein or using a vector comprising said DNA, or using a transformant obtained by transforming host cells with said vector.

9. An affinity separation matrix, comprising:
   the protein according to claim 1 as an affinity ligand; and
   a carrier made of a water-insoluble base material on which the protein is immobilized.

10. The affinity separation matrix according to claim 9, wherein the affinity separation matrix binds to a protein containing an Fc region of an immunoglobulin.

11. The affinity separation matrix according to claim 10, wherein the protein containing an Fc region of an immunoglobulin is an immunoglobulin G or an immunoglobulin G derivative.

12. A method for producing the affinity separation matrix according to claim 9, the method comprising
   immobilizing a protein comprising three or more amino acid sequences derived from any domain selected from E, D, A, B, and C domains of Protein A, the amino acid sequences comprising amino acid substitutions for all lysine residues (Lys) in the domains,
   wherein the amino acid sequences are connected to one another through one or more linkers,
   wherein (i) at least two of the linkers contain a lysine residue (Lys) or a cysteine residue (Cys), or
   (ii) at least one of the linkers contains a lysine residue or a cysteine residue, and a region within 4 or less residues from N- or C-terminus of the protein comprises a lysine residue or a cysteine residue,
   at least 90% of the following amino acid residues: Gln-9, Gln-10, Phe-13, Tyr-14, Leu-17, Pro-20, Asn-21, Leu-22, Gln-26, Arg-27, Phe-30, Ile-31, Leu-34, Pro-38, Ser-39, Leu-45, Leu-51, Asn-52, Gln-55, and Pro-57 (the residue numbers indicated are corresponding residue numbers of the C domain and the positions of the conserved amino acids for any domain selected from E, D, A and B domains are respectively compared to the C domain positions upon alignment with the C domain of any domain selected from E, D, A and B domains) are conserved in any domain selected from E, D, A, B, and C domains in the protein, and
   the amino acid sequences having at least 80% sequence identity to the amino acid sequences of the E, D, A, B, or C domains before the lysine substitutions
   on a carrier made of a water-insoluble base material.

13. A method for purifying a protein containing an Fc region of an immunoglobulin, the method comprising
   adsorbing the protein containing an Fc region of an immunoglobulin to the affinity separation matrix according to claim 9.

14. The protein according to claim 2,
   wherein the amino acid sequences before the substitutions are any of the amino acid sequences of SEQ ID NOs:1 to 5 or any of the amino acid sequences of SEQ ID NOs:1 to 5 comprising at least one of the following mutations (1) to (4):

(1) a substitution of Ala, Val, Leu, Ile, Phe, Tyr, Trp, Thr, Ser, Asp, Glu, Arg, His, or Met for an amino acid residue in the domain corresponding to position 29 of the C domain;
(2) a substitution of Leu, Ile, Phe, Tyr, Trp, Thr, Asp, Glu, Asn, Gln, Arg, His, or Met for an amino acid residue in the domain corresponding to position 33 of the C domain;
(3) a substitution of Leu, Ile, Phe, Tyr, Trp, Glu, Arg, His, or Met for an amino acid residue in the domain corresponding to position 36 of the C domain; and
(4) a substitution of Leu, Ile, Phe, Tyr, Trp, Glu, Arg, His, or Met for an amino acid residue in the domain corresponding to position 37 of the C domain.

* * * * *

SEQUENCE LISTING

<160> NUMBER OF SEQ ID NOS: 26

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

```
Lys Lys Leu Asn Asp Ala Gln Ala Pro Lys
     50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
     50                  55

<210> SEQ ID NO 6
<211> LENGTH: 58
<212> TYPE: PRT
<213> ORGANISM: Artificial
<220> FEATURE:
<223> OTHER INFORMATION: Zdomain

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 7
<211> LENGTH: 58
<212> TYPE: PRT
<213> ORGANISM: Artificial
<220> FEATURE:
<223> OTHER INFORMATION: SpA C domain mutant

<400> SEQUENCE: 7

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
        35                  40                  45

Gln Arg Leu Asn Asp Ala Gln Ala Pro Lys
     50                  55

<210> SEQ ID NO 8
<211> LENGTH: 290
<212> TYPE: PRT
<213> ORGANISM: Artificial
<220> FEATURE:
<223> OTHER INFORMATION: SpA C domain mutant

<400> SEQUENCE: 8

Ala Asp Asn Arg Phe Asn Arg Glu Gln Gln Asn Ala Phe Tyr Glu Ile
1               5                   10                  15
```

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
            35                  40                  45

Gln Arg Leu Asn Asp Ala Gln Ala Pro Lys Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Arg Leu Arg Asp Asp Pro
                 85                  90                  95

Ser Val Ser Arg Glu Ile Leu Ala Glu Ala Gln Arg Leu Asn Asp Ala
            100                 105                 110

Gln Ala Pro Lys Ala Asp Asn Arg Phe Asn Arg Glu Gln Gln Asn Ala
            115                 120                 125

Phe Tyr Glu Ile Leu His Leu Pro Asn Leu Thr Glu Glu Gln Arg Asn
            130                 135                 140

Ala Phe Ile Gln Arg Leu Arg Asp Asp Pro Ser Val Ser Arg Glu Ile
145                 150                 155                 160

Leu Ala Glu Ala Gln Arg Leu Asn Asp Ala Gln Ala Pro Lys Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Glu Gln Arg Asn Ala Phe Ile Gln Arg Leu
            195                 200                 205

Arg Asp Asp Pro Ser Val Ser Arg Glu Ile Leu Ala Glu Ala Gln Arg
        210                 215                 220

Leu Asn Asp Ala Gln Ala Pro Lys Ala Asp Asn Arg Phe Asn Arg Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Arg Leu Arg Asp Asp Pro Ser Val
            260                 265                 270

Ser Arg Glu Ile Leu Ala Glu Ala Gln Arg Leu Asn Asp Ala Gln Ala
            275                 280                 285

Pro Lys
    290

<210> SEQ ID NO 9
<211> LENGTH: 232
<212> TYPE: PRT
<213> ORGANISM: Artificial
<220> FEATURE:
<223> OTHER INFORMATION: SpA C domain mutant

<400> SEQUENCE: 9

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
            35                  40                  45

Gln Arg Leu Asn Asp Ala Gln Ala Pro Lys Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Arg Leu Arg Asp Asp Pro
                    85                  90                  95

Ser Val Ser Arg Glu Ile Leu Ala Glu Ala Gln Arg Leu Asn Asp Ala
                100                 105                 110

Gln Ala Pro Lys Ala Asp Asn Arg Phe Asn Arg Glu Gln Gln Asn Ala
                115                 120                 125

Phe Tyr Glu Ile Leu His Leu Pro Asn Leu Thr Glu Glu Gln Arg Asn
130                 135                 140

Ala Phe Ile Gln Arg Leu Arg Asp Asp Pro Ser Val Ser Arg Glu Ile
145                 150                 155                 160

Leu Ala Glu Ala Gln Arg Leu Asn Asp Ala Gln Ala Pro Lys Ala Asp
                165                 170                 175

Asn Arg Phe Asn Arg Glu Gln Gln Asn Ala Phe Tyr Glu Ile Leu His
                180                 185                 190

Leu Pro Asn Leu Thr Glu Glu Gln Arg Asn Ala Phe Ile Gln Arg Leu
                195                 200                 205

Arg Asp Asp Pro Ser Val Ser Arg Glu Ile Leu Ala Glu Ala Gln Arg
                210                 215                 220

Leu Asn Asp Ala Gln Ala Pro Lys
225                 230

<210> SEQ ID NO 10
<211> LENGTH: 232
<212> TYPE: PRT
<213> ORGANISM: Artificial
<220> FEATURE:
<223> OTHER INFORMATION: SpA C domain mutant

<400> SEQUENCE: 10

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Arg Leu Arg Asp Asp Pro Ser Val Ser Arg Glu Ile Leu Ala Glu Ala
                35                  40                  45

Gln Arg Leu Asn Asp Ala Gln Ala Pro Lys Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Arg Leu Arg Asp Asp Pro
                85                  90                  95

Ser Val Ser Arg Glu Ile Leu Ala Glu Ala Gln Arg Leu Asn Asp Ala
                100                 105                 110

Gln Ala Pro Lys Ala Asp Asn Arg Phe Asn Arg Glu Gln Gln Asn Ala
                115                 120                 125

Phe Tyr Glu Ile Leu His Leu Pro Asn Leu Thr Glu Glu Gln Arg Asn
130                 135                 140

Ala Phe Ile Gln Arg Leu Arg Asp Asp Pro Ser Val Ser Arg Glu Ile
145                 150                 155                 160

Leu Ala Glu Ala Gln Arg Leu Asn Asp Ala Gln Ala Pro Lys Ala Asp
                165                 170                 175

Asn Arg Phe Asn Arg Glu Gln Gln Asn Ala Phe Tyr Glu Ile Leu His
                180                 185                 190

Leu Pro Asn Leu Thr Glu Glu Gln Arg Asn Ala Phe Ile Gln Arg Leu
                195                 200                 205

Arg Asp Asp Pro Ser Val Ser Arg Glu Ile Leu Ala Glu Ala Gln Arg
    210                 215                 220

Leu Asn Asp Ala Gln Ala Pro Arg
225                 230

<210> SEQ ID NO 11
<211> LENGTH: 896
<212> TYPE: DNA
<213> ORGANISM: Artificial
<220> FEATURE:
<223> OTHER INFORMATION: Code DNA

<400> SEQUENCE: 11
ccatggcttt cgctgcagat aaccgtttta accgtgaaca acaaaacgct ttctacgaaa      60
tcctgcactt gccaaacctt actgaagaac aacgtaatgc tttcatccaa cgtctgcgcg     120
atgatccatc tgtatcccgt gaaattttgg cagaggctca acgacttaac gacgctcagg     180
cgcctaaggc tgataaccgc ttcaaccgag aacaacaaaa cgcttttttat gaaatccttc    240 acctgccaaa tcttacagaa gaacaacgca acgcattcat tcaacgcttg cgtgatgacc    300
cttccgttag ccgagagatc ctggctgaag cacaacgttt gaatgatgcg caagcaccaa    360
aagctgataa tcgattcaac cgtgaacaac aaaatgcatt ctacgaaatc ttgcaccttc    420
ctaacctgac tgaagagcag cgtaacgctt ttatccagcg tttgagagac gatccatctg    480
tctcccgtga aattctcgca gaagcgcaac gcctgaacga tgctcaagct ccgaaagcag    540
acaaccgttt caatcgcgaa cagcaaaacg cgttttatga aattctgcat cttccaaact    600
tgacagagga acaacgcaat gctttcatcc aacgactgcg tgatgatccg agcgtttctc    660
gagaaatctt ggctgaagca caacgtctga cgacgctca agctccaaaa gcggataaca    720
gatttaaccg tgaacaacaa aatgctttct acgagatctt gcaccttccg aacctgactg    780
aagaacaacg taacgcattt attcagagat tgcgcgatga cccatccgta agccgtgaga    840
tcctggcaga agctcaacgt ttgaatgatg cacaagctcc aaaataatct agaaaa        896

<210> SEQ ID NO 12
<211> LENGTH: 29
<212> TYPE: DNA
<213> ORGANISM: Artificial
<220> FEATURE:
<223> OTHER INFORMATION: synthetic oligonucleotide

<400> SEQUENCE: 12
ctcccatggc tttcgctgca gataaccgc                                        29

<210> SEQ ID NO 13
<211> LENGTH: 34
<212> TYPE: DNA
<213> ORGANISM: Artificial
<220> FEATURE:
<223> OTHER INFORMATION: synthetic oligonucleotide

<400> SEQUENCE: 13
ttttctagat tattttggag cttgtgcatc attc                                  34

<210> SEQ ID NO 14
<211> LENGTH: 725
<212> TYPE: DNA
<213> ORGANISM: Artificial
<220> FEATURE:
<223> OTHER INFORMATION: Code DNA

<400> SEQUENCE: 14

```
ctcccatggc tttcgctgca gataaccgct tcaaccgaga acaacaaaac gcttttatg      60
aaatccttca cctgccaaat cttacagaag aacaacgcaa cgcattcatt caacgcttgc    120
gtgatgaccc ttccgttagc cgagagatcc tggctgaagc acaacgtttg aatgatgcgc    180
aagcaccaaa agctgataat cgattcaacc gtgaacaaca aaatgcattc tacgaaatct    240
tgcaccttcc taacctgact gaagagcagc gtaacgcttt tatccagcgt ttgagagacg    300
atccatctgt ctcccgtgaa attctcgcag aagcgcaacg cctgaacgat gctcaagctc    360
cgaaagcaga caaccgtttc aatcgcgaac agcaaaacgc gttttatgaa attctgcatc    420
ttccaaactt gacagaggaa caacgcaatg ctttcatcca acgactgcgt gatgatccga    480
gcgtttctcg agaaatcttg gctgaagcac aacgtctgaa cgacgctcaa gctccaaaag    540
cggataacag atttaaccgt gaacaacaaa atgctttcta cgagatcttg caccttccga    600
acctgactga agaacaacgt aacgcattta ttcagagatt gcgcgatgac ccatccgtaa    660
gccgtgagat cctggcagaa gctcaacgtt tgaatgatgc acaagctcca aaataatcta    720
gaaaa                                                                 725
```

<210> SEQ ID NO 15
<211> LENGTH: 34
<212> TYPE: DNA
<213> ORGANISM: Artificial
<220> FEATURE:
<223> OTHER INFORMATION: synthetic oligonucleotide

<400> SEQUENCE: 15

```
ttttctagat taacgtggag cttgtgcatc attc                                  34
```

<210> SEQ ID NO 16
<211> LENGTH: 725
<212> TYPE: DNA
<213> ORGANISM: Artificial
<220> FEATURE:
<223> OTHER INFORMATION: Code DNA

<400> SEQUENCE: 16

```
ctcccatggc tttcgctgca gataaccgct tcaaccgaga acaacaaaac gcttttatg      60
aaatccttca cctgccaaat cttacagaag aacaacgcaa cgcattcatt caacgcttgc    120
gtgatgaccc ttccgttagc cgagagatcc tggctgaagc acaacgtttg aatgatgcgc    180
aagcaccaaa agctgataat cgattcaacc gtgaacaaca aaatgcattc tacgaaatct    240
tgcaccttcc taacctgact gaagagcagc gtaacgcttt tatccagcgt ttgagagacg    300
atccatctgt ctcccgtgaa attctcgcag aagcgcaacg cctgaacgat gctcaagctc    360
cgaaagcaga caaccgtttc aatcgcgaac agcaaaacgc gttttatgaa attctgcatc    420
ttccaaactt gacagaggaa caacgcaatg ctttcatcca acgactgcgt gatgatccga    480
gcgtttctcg agaaatcttg gctgaagcac aacgtctgaa cgacgctcaa gctccaaaag    540
cggataacag atttaaccgt gaacaacaaa atgctttcta cgagatcttg caccttccga    600
acctgactga agaacaacgt aacgcattta ttcagagatt gcgcgatgac ccatccgtaa    660
gccgtgagat cctggcagaa gctcaacgtt tgaatgatgc acaagctcca cgttaatcta    720
gaaaa                                                                 725
```

<210> SEQ ID NO 17
<211> LENGTH: 58

```
<212> TYPE: PRT
<213> ORGANISM: Artificial
<220> FEATURE:
<223> OTHER INFORMATION: SpA C domain mutant

<400> SEQUENCE: 17

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45

Arg Arg Leu Asn Asp Ala Gln Ala Pro Lys
    50                  55

<210> SEQ ID NO 18
<211> LENGTH: 174
<212> TYPE: PRT
<213> ORGANISM: Artificial
<220> FEATURE:
<223> OTHER INFORMATION: SpA C domain mutant

<400> SEQUENCE: 18

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45

Arg Arg Leu Asn Asp Ala Gln Ala Pro Lys Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Leu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Leu Leu Arg Asp Asp Pro Ser Val Ser Arg Glu Ile
145                 150                 155                 160

Leu Ala Glu Ala Arg Arg Leu Asn Asp Ala Gln Ala Pro Lys
                165                 170

<210> SEQ ID NO 19
<211> LENGTH: 551
<212> TYPE: DNA
<213> ORGANISM: Artificial
<220> FEATURE:
<223> OTHER INFORMATION: Code DNA

<400> SEQUENCE: 19
ctcccatggc tttcgctgca gacaaccgtt tcaatcgcga acagcaaaac gcgtttatg      60 aaattctgca tcttccaaac ttgacagagg aacaacgcaa tgctttcatc caactgctgc    120
gtgatgatcc gagcgtttct cgtgaaatct tggctgaagc acgtcgcctg aacgacgctc    180
aagctccaaa agcggataac cgttttaacc gtgaacaaca aaatgctttc tacgagatct    240
```

```
tgcaccttcc gaacctgact gaagaacaac gtaacgcatt tattcagttg ttgcgtgatg    300
acccatccgt aagccgcgag atcctggcag aagctcgccg cttgaatgat gcacaagctc    360
caaaagcaga caaccgcttt aaccgcgaac aacaaaatgc attctacgaa atcttgcacc    420
ttcctaacct gactgaggag caacgcaatg ctttcatcca attgcttcgc gatgatccaa    480
gcgtaagccg tgaaattttg gctgaagctc gtcgtctgaa cgatgcacaa gctccaaaat    540
aatctagaaa a                                                         551
```

<210> SEQ ID NO 20
<211> LENGTH: 290
<212> TYPE: PRT
<213> ORGANISM: Artificial
<220> FEATURE:
<223> OTHER INFORMATION: SpA C domain mutant

<400> SEQUENCE: 20

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Glu Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Glu Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Glu Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290
```

<210> SEQ ID NO 21
<211> LENGTH: 870
<212> TYPE: DNA
<213> ORGANISM: Artificial
<220> FEATURE:
<223> OTHER INFORMATION: Code DNA

<400> SEQUENCE: 21

| | | | | | |
|---|---|---|---|---|---|
| gcagataaca | aatttaacaa | agaacaacaa | aacgctttct | acgaaatcct | gcacttgcca | 60 |
| aaccttactg | aagaacaacg | taatgctttc | atccaagagc | tgaaagatga | tccatctgta | 120 |
| tccaagaaa | ttttggcaga | ggctaaaaaa | cttaacgacg | ctcaggcgcc | taaggctgat | 180 |
| aacaaattca | acaagaaca | acaaaacgct | ttttatgaaa | tccttcacct | gccaaatctt | 240 |
| acagaagaac | aacgcaacgc | attcattcaa | gagttgaagg | atgacccttc | cgttagcaaa | 300 |
| gagatcctgg | ctgaagcaaa | aaagttgaat | gatgcgcaag | caccaaaagc | tgataataaa | 360 |
| ttcaacaaag | aacaacaaaa | tgcattctac | gaaatcttgc | accttcctaa | cctgactgaa | 420 |
| gagcagcgta | acgcttttat | ccaggaattg | aaagacgatc | catctgtctc | caagaaatt | 480 |
| ctcgcagaag | cgaagaaact | gaacgatgct | caagctccga | agcagacaa | caattcaat | 540 |
| aaggaacagc | aaaacgcgtt | ttatgaaatt | ctgcatcttc | caaacttgac | agaggaacaa | 600 |
| cgcaatgctt | tcatccaaga | gctgaaagat | gatccgagcg | tttctaagga | aatcttggct | 660 |
| gaagcaaaaa | aactgaacga | cgctcaagct | ccaaaagcgg | ataacaagtt | taacaaagaa | 720 |
| caacaaaatg | ctttctacga | gatcttgcac | cttccgaacc | tgactgaaga | caacgtaac | 780 |
| gcatttattc | aggagttgaa | ggatgaccca | tccgtaagca | aagagatcct | ggcagaagct | 840 |
| aaaaaattga | atgatgcaca | agctccaaaa | | | | 870 |

<210> SEQ ID NO 22
<211> LENGTH: 174
<212> TYPE: PRT
<213> ORGANISM: Artificial
<220> FEATURE:
<223> OTHER INFORMATION: SpA C domain mutant

<400> SEQUENCE: 22

Ala Asp Asn Arg Phe Asn Arg Glu Gln Gln Asn Ala Phe Tyr Glu Ile
1               5                  10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Leu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Leu Leu Arg Asp Asp Pro Ser Val Ser Arg Glu Ile

Leu Ala Glu Ala Arg Arg Leu Asn Asp Ala Gln Ala Pro Lys
            165                 170

<210> SEQ ID NO 23
<211> LENGTH: 522
<212> TYPE: DNA
<213> ORGANISM: Artificial
<220> FEATURE:
<223> OTHER INFORMATION: Code DNA

<400> SEQUENCE: 23

```
gcagacaacc gtttcaatcg cgaacagcaa aacgcgtttt atgaaattct gcatcttcca    60
aacttgacag aggaacaacg caatgctttc atccaactgc tgcgtgatga tccgagcgtt   120
tctcgtgaaa tcttggctga agcacgtcgc ctgaacgacg ctcaagctcc acgcgcggat   180
aaccgtttta accgtgaaca acaaaatgct ttctacgaga tcttgcacct tccgaacctg   240
actgaagaac aacgtaacgc atttattcag ttgttgcgtg atgacccatc cgtaagccgc   300
gagatcctgg cagaagctcg ccgcttgaat gatgcacaag ctccacgcgc agacaaccgc   360
tttaaccgcg aacaacaaaa tgcattctac gaaatcttgc accttcctaa cctgactgag   420
gagcaacgca atgctttcat ccaattgctt cgcgatgatc caagcgtaag ccgtgaaatt   480
ttggctgaag ctcgtcgtct gaacgatgca caagctccaa aa                     522
```

<210> SEQ ID NO 24
<211> LENGTH: 58
<212> TYPE: PRT
<213> ORGANISM: Artificial
<220> FEATURE:
<223> OTHER INFORMATION: SpA C domain mutant

<400> SEQUENCE: 24

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
        35                  40                  45

Gln Arg Leu Asn Asp Ala Gln Ala Pro Arg
    50                  55

<210> SEQ ID NO 25
<211> LENGTH: 290
<212> TYPE: PRT
<213> ORGANISM: Artificial
<220> FEATURE:
<223> OTHER INFORMATION: SpA C domain mutant

<400> SEQUENCE: 25

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Arg Leu Arg Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Arg Leu Arg Asp Asp Pro
                85                  90                  95

Ser Val Ser Arg Glu Ile Leu Ala Glu Ala Gln Arg Leu Asn Asp Ala
            100                 105                 110

Gln Ala Pro Arg Ala Asp Asn Arg Phe Asn Arg Glu Gln Gln Asn Ala
        115                 120                 125

Phe Tyr Glu Ile Leu His Leu Pro Asn Leu Thr Glu Gln Arg Asn
    130                 135                 140

Ala Phe Ile Gln Arg Leu Arg Asp Asp Pro Ser Val Ser Arg Glu Ile
145                 150                 155                 160

Leu Ala Glu Ala Gln Arg Leu Asn Asp Ala Gln Ala Pro Arg Ala Asp
                165                 170                 175

Asn Arg Phe Asn Arg Glu Gln Gln Asn Ala Phe Tyr Glu Ile Leu His
            180                 185                 190

Leu Pro Asn Leu Thr Glu Gln Arg Asn Ala Phe Ile Gln Arg Leu
        195                 200                 205

Arg Asp Asp Pro Ser Val Ser Arg Glu Ile Leu Ala Glu Ala Gln Arg
    210                 215                 220

Leu Asn Asp Ala Gln Ala Pro Arg Ala Asp Asn Arg Phe Asn Arg Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Arg Leu Arg Asp Asp Pro Ser Val
            260                 265                 270

Ser Arg Glu Ile Leu Ala Glu Ala Gln Arg Leu Asn Asp Ala Gln Ala
        275                 280                 285

Pro Lys
    290

<210> SEQ ID NO 26
<211> LENGTH: 893
<212> TYPE: DNA
<213> ORGANISM: Artificial
<220> FEATURE:
<223> OTHER INFORMATION: Code DNA

<400> SEQUENCE: 26
ccatggcttt cgctgcagat aaccgtttta accgtgaaca acaaaacgct ttctacgaaa      60
tcctgcactt gccaaacctt actgaagaac aacgtaatgc tttcatccaa cgtctgcgcg     120
atgatccatc tgtatcccgt gaaattttgg cagaggctca acgacttaac gacgctcagg     180
cgcctcgcgc tgataaccgc ttcaaccgag aacaacaaaa cgcttttat gaaatccttc      240 acctgccaaa tcttacagaa gaacaacgca acgcattcat tcaacgcttg cgtgatgacc     300
cttccgttag ccgagagatc ctggctgaag cacaacgttt gaatgatgcg caagcaccac     360
gtgctgataa tcgattcaac cgtgaacaac aaaatgcatt ctacgaaatc ttgcaccttc     420
ctaacctgac tgaagagcag cgtaacgctt ttatccagcg tttgagagac gatccatctg     480
tctcccgtga aattctcgca gaagcgcaac gcctgaacga tgctcaagct ccgcgtgcag     540
acaaccgttt caatcgcgaa cagcaaaacg cgttttatga aattctgcat cttccaaact     600
tgacagagga acaacgcaat gctttcatcc aacgactgcg tgatgatccg agcgtttctc     660

```
gagaaatctt ggctgaagca caacgtctga acgacgctca agctccacga gcggataaca      720
gatttaaccg tgaacaacaa aatgctttct acgagatctt gcaccttccg aacctgactg      780
aagaacaacg taacgcattt attcagagat tgcgcgatga cccatccgta agccgtgaga      840
tcctggcaga agctcaacgt ttgaatgatg cacaagctcc aaaataatct aga             893
```